US009322069B2

(12) United States Patent
De Beuckeleer

(10) Patent No.: US 9,322,069 B2
(45) Date of Patent: Apr. 26, 2016

(54) ELITE EVENT A2704-12 AND METHODS AND KITS FOR IDENTIFYING SUCH EVENT IN BIOLOGICAL SAMPLES

(75) Inventor: Marc De Beuckeleer, Zwijnaarde (BE)

(73) Assignee: Bayer CropScience N.V., Diegem (BE)

( * ) Notice: Subject to any disclaimer, the term of this patent is extended or adjusted under 35 U.S.C. 154(b) by 223 days.

(21) Appl. No.: 13/196,705

(22) Filed: Aug. 2, 2011

(65) Prior Publication Data

US 2011/0294127 A1    Dec. 1, 2011

Related U.S. Application Data

(62) Division of application No. 11/910,899, filed as application No. PCT/EP2006/003454 on Apr. 4, 2006, now Pat. No. 8,012,689.

(60) Provisional application No. 60/670,213, filed on Apr. 11, 2005.

(30) Foreign Application Priority Data

Apr. 8, 2005 (EP) .................................... 05075833

(51) Int. Cl.
*C12Q 1/68* (2006.01)
*C12P 19/34* (2006.01)
*C07H 21/04* (2006.01)
*C12N 15/82* (2006.01)

(52) U.S. Cl.
CPC .......... *C12Q 1/6895* (2013.01); *C12N 15/8277* (2013.01)

(58) Field of Classification Search
USPC .............................. 435/91.2, 6.12; 536/24.33
See application file for complete search history.

(56) References Cited

U.S. PATENT DOCUMENTS

| | | |
|---|---|---|
| 5,576,477 A | 11/1996 | Matson et al. |
| 5,824,850 A | 10/1998 | Rhodes et al. |
| 5,965,138 A | 10/1999 | Cochran et al. |
| 6,177,617 B1 | 1/2001 | Matson et al. |
| 6,180,391 B1 | 1/2001 | Brown |
| 6,376,754 B1 | 4/2002 | Schillinger et al. |
| 6,395,966 B1 | 5/2002 | Mumm et al. |
| 6,468,747 B1 | 10/2002 | De Beuckeleer et al. |
| 2001/0049125 A1 | 12/2001 | Stemmer et al. |
| 2002/0073443 A1 | 6/2002 | Heifetz et al. |
| 2004/0031072 A1* | 2/2004 | La Rosa et al. ............... 800/278 |
| 2011/0294127 A1* | 12/2011 | De Beuckeleer ............ 435/6.12 |

FOREIGN PATENT DOCUMENTS

| | | |
|---|---|---|
| CN | 1 470 643 A | 1/2004 |
| CN | 1 485 439 A | 3/2004 |
| WO | 9928483 * | 6/1999 |
| WO | WO 00/26356 | 5/2000 |
| WO | WO 02/27322 | 4/2002 |
| WO | WO 03/097790 | 11/2003 |

OTHER PUBLICATIONS

Lowe et al. Nucleic acid research, 1990, vol. 18(7), p. 1757-1761.*
Nucleic acid sequence search reports, AC: AFO83366, AX021180 and ABX16109.*
De Block, et al. (1987) EMBO Journal 6: 2512-2518.
Edwards, et al. (1991) Nucleic Acids Research 19: 1349.
Liu, et al. (1995) Plant Journal 8(3); 457-463.
Wilbur and Lipmann (1983) Proceeding of the National Academy of Sciences USA 80(3): 726-730.
International Search Report for International Application No. PCT/EP2006/003454, mailed Octobtr 6, 2006.
Written Opinion for International Application No. PCT/EP2006/003454, mailed Oct. 6, 2006.

* cited by examiner

*Primary Examiner* — Kenneth R. Horlick
*Assistant Examiner* — Joyce Tung
(74) *Attorney, Agent, or Firm* — Arent Fox LLP

(57) ABSTRACT

Tools are provided which allow rapid and unequivocal identification elite event A207-12 in biological samples.

22 Claims, 2 Drawing Sheets

ELITE EVENT A2704-12 AND METHODS AND KITS FOR IDENTIFYING SUCH EVENT IN BIOLOGICAL SAMPLES

CROSS-REFERENCE TO RELATED APPLICATIONS

This application is a Divisional of U.S. application Ser. No. 11/910,899, filed Oct. 5, 2007, which is the U.S. National Stage filing of International Application No. PCT/EP2006/003454, filed Apr. 4, 2006, which claims priority to EP05075833.3, filed Apr. 8, 2005, and U.S. Provisional Patent Application No. 60/670,213, filed Apr. 11, 2005; the disclosures of each of which are hereby incorporated by reference.

FIELD OF THE INVENTION

This invention pertains to methods and kits for identifying in biological samples the presence of plant material comprising specifically transformation event A2704-12, as well as transgenic soybean plants, plant material and seeds containing such event. The soybean plants of the invention combine the herbicide tolerant phenotype with an agronomic performance, genetic stability and adaptability to different genetic backgrounds equivalent to the non-transformed soybean line in the absence of weed pressure.

BACKGROUND OF THE INVENTION

The phenotypic expression of a transgene in a plant is determined both by the structure of the gene itself and by its location in the plant genome. At the same time the presence of the transgene (in a foreign DNA) at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials, eventually leading to the selection of an elite event.

The unequivocal identification of an elite event is becoming increasingly important in view of discussions on Novel Food/Feed, segregation of GMO and non-GMO products and the identification of proprietary material. Ideally, such identification method is both quick and simple, without the need for an extensive laboratory set-up. Furthermore, the method should provide results that allow unequivocal determination of the elite event without expert interpretation, but which hold up under expert scrutiny if necessary.

A2704-12 was selected as an elite event in the development of soybean (*Glycine max* L.) resistant to the herbicide Liberty®, by transformation of soybean with a plasmid comprising the synthetic pat gene encoding tolerance to phosphinothricin and may be commercially sold as Liberty Link® soybean. The tools for use in simple and unequivocal methods for identification elite event A2704-12 in biological samples are described herein.

SUMMARY OF THE INVENTION

The present invention relates to methods for identifying elite event A2704-12 in biological samples, which methods are based on primers or probes which specifically recognize the 5' and/or 3' flanking sequence of A2704-12.

More specifically, the invention relates to a method comprising of amplifying a sequence of a nucleic acid present in biological samples, using a polymerase chain reaction with at least two primers, one of which recognizes the 5' or 3' flanking region of A2704-12, the other which recognizes a sequence within the foreign DNA, preferably to obtain a DNA fragment of between 100 and 500 bp. The primers may recognize a sequence within the 5' flanking region of A2704-12 (SEQ ID No. 1, from position 1 to position 209) or within the 3' flanking region of A2704-12 (complement of SEQ ID No 2 from position 569 to position 1000) and a sequence within the foreign DNA (complement of SEQ ID No 1 from position 210 to 720 or SEQ ID No 2 from position 1 to position 568), respectively. The primer recognizing the 5' flanking region may comprise the nucleotide sequence of SEQ ID No. 4 and the primer recognizing a sequence within the foreign DNA may comprise the nucleotide sequence of SEQ ID No. 8 described herein.

The present invention more specifically relates to a method for identifying elite event A2704-12 in biological samples, which method comprises amplifying a sequence of a nucleic acid present in a biological sample, using a polymerase chain reaction with two primers having the nucleotide sequence of SEQ ID No. 4 and SEQ ID No. 8 respectively, to obtain a DNA fragment of about 185 bp.

The present invention further relates to the specific flanking sequences of A2704-12 described herein, which can be used to develop specific identification methods for A2704-12 in biological samples. More particularly, the invention relates to the 5' and or 3' flanking regions of A2704-12 which can be used for the development of specific primers and probes as further described herein. The invention further relates to identification methods for the presence of A2704-12 in biological samples based on the use of such specific primers or probes. Primers may consist of a nucleotide sequence of 17 to about 200 consecutive nucleotides selected from the nucleotide sequence of SEQ ID No 1 from nucleotide 1 to nucleotide 209 or the complement of the nucleotide sequence of SEQ ID 2 from nucleotide 569 to nucleotide 1000) combined with primers consisting of a nucleotide sequence of 17 to about 200 consecutive nucleotides selected from the complement of the nucleotide sequence of SEQ ID No 1 from nucleotide 210 to nucleotide 720 or the nucleotide sequence of SEQ ID No 2 from nucleotide 1 to nucleotide 569. Primers may also comprise these nucleotide sequences located at their extreme 3' end, and further comprise unrelated sequences or sequences derived from the mentioned nucleotide sequences, but comprising mismatches.

The invention further relates to kits for identifying elite event A2704-12 in biological samples, said kits comprising at least one primer or probe which specifically recognizes the 5' or 3' flanking region of A2704-12.

The kit of the invention may comprise, in addition to a primer which specifically recognizes the 5' or 3' flanking region of A2704-12, a second primer which specifically recognizes a sequence within the foreign DNA of A2704-12, for use in a PCR identification protocol. Preferably, the kit of the invention comprises two specific primers, one of which recognizes a sequence within the 5' flanking region of A2704-12, and the other which recognizes a sequence within the foreign DNA. Especially The primer recognizing the 5' flanking region may comprises the nucleotide sequence of SEQ ID No. 4 and the primer recognizing the transgene may comprises the nucleotide sequence of SEQ ID No. 8 or any other primer as described herein.

The invention further relates to a kit for identifying elite event A2704-12 in biological samples, said kit comprising the PCR primers having the nucleotide sequence of SEQ ID No. 4 and SEQ ID No. 8 for use in the A2704-12 PCR identification protocol described herein.

The invention also relates to a kit for identifying elite event A2704-12 in biological samples, which kit comprises a specific probe having a sequence which corresponds (or is complementary to) a sequence having between 80% and 100% sequence identity with a specific region of A2704-12. Preferably the sequence of the probe corresponds to a specific region comprising part of the 5' or 3' flanking region of A2704-12. Most preferably the specific probe has (or is complementary to) a sequence having between 80% and 100% sequence identity to the sequence between nucleotide 160 and 260 of SEQ ID No. 1 or the sequence between nucleotide 520 and 620 of SEQ ID No 2.

The methods and kits encompassed by the present invention can be used for different purposes such as, but not limited to the following: to identify the presence or absence of A2704-12 in plants, plant material or in products such as, but not limited to food or feed products (fresh or processed) comprising or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality (i.e. percentage pure material) of plant material comprising A2704-12.

The invention further relates to the 5' and/or 3' flanking regions of A2704-12 as well as to the specific primers and probes developed from the 5' and/or 3' flanking sequences of A2704-12.

The invention also relates to soybean plants, parts thereof, cells, seeds and progeny plants comprising elite event A2704-12. Such plants, parts thereof, cells, seeds and progeny plants can be identified using the methods as herein described.

DETAILED DESCRIPTION

The incorporation of a recombinant DNA molecule in the plant genome typically results from transformation of a cell or tissue (or from another genetic manipulation). The particular site of incorporation is either due to "random" integration or is at a predetermined location (if a process of targeted integration is used).

The DNA introduced into the plant genome as a result of transformation of a plant cell or tissue with a recombinant DNA or "transforming DNA", and originating from such transforming DNA is hereinafter referred to as "foreign DNA" comprising one or more "transgenes". "Plant DNA" in the context of the present invention will refer to DNA originating from the plant which is transformed. Plant DNA will usually be found in the same genetic locus in the corresponding wild-type plant. The foreign DNA can be characterized by the location and the configuration at the site of incorporation of the recombinant DNA molecule in the plant genome. The site in the plant genome where a recombinant DNA has been inserted is also referred to as the "insertion site" or "target site". Insertion of the recombinant DNA into the plant genome can be associated with a deletion of plant DNA, referred to as "target site deletion". A "flanking region" or "flanking sequence" as used herein refers to a sequence of at least 20 bp, preferably at least 50 bp, and up to 5000 bp of the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the recombinant DNA is introduced into a plant through traditional crossing, its insertion site in the plant genome, or its flanking regions will generally not be changed. An "insertion region" as used herein refers to the region corresponding to the region of at least 40 bp, preferably at least 100 bp, and up to 10000 bp, encompassed by the sequence which comprises the upstream and/or the downstream flanking region of a foreign DNA in the plant genome. Taking into consideration minor differences due to mutations within a species, an insertion region will retain, upon crossing into a plant of the same species, at least 85%, preferably 90%, more preferably 95%, and most preferably 100% sequence identity with the sequence comprising the upstream and downstream flanking regions of the foreign DNA in the plant originally obtained from transformation.

An event is defined as a (artificial) genetic locus that, as a result of genetic engineering, carries a transgene comprising at least one copy of a gene of interest. The typical allelic states of an event are the presence or absence of the foreign DNA. An event is characterized phenotypically by the expression of the transgene. At the genetic level, an event is part of the genetic makeup of a plant. At the molecular level, an event can be characterized by the restriction map (e.g. as determined by Southern blotting), by the upstream and/or downstream flanking sequences of the transgene, the location of molecular markers and/or the molecular configuration of the transgene. Usually transformation of a plant with a transforming DNA comprising at least one gene of interest leads to a multitude of events, each of which is unique.

An elite event, as used herein, is an event which is selected from a group of events, obtained by transformation with the same transforming DNA or by back-crossing with plants obtained by such transformation, based on the expression and stability of the transgene(s) and its compatibility with optimal agronomic characteristics of the plant comprising it. Thus the criteria for elite event selection are one or more, preferably two or more, advantageously all of the following:

a) That the presence of the foreign DNA does not compromise other desired characteristics of the plant, such as those relating to agronomic performance or commercial value;

b) That the event is characterized by a well defined molecular configuration which is stably inherited and for which appropriate tools for identity control can be developed;

c) That the gene(s) of interest show(s) a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use.

It is preferred that the foreign DNA is associated with a position in the plant genome that allows easy introgression into desired commercial genetic backgrounds.

The status of an event as an elite event is confirmed by introgression of the elite event in different relevant genetic backgrounds and observing compliance with one, two or all of the criteria e.g. a), b) and c) above.

An "elite event" thus refers to a genetic locus comprising a foreign DNA, which answers to the above-described criteria. A plant, plant material or progeny such as seeds can comprise one or more elite events in its genome.

The tools developed to identify an elite event or the plant, plant material comprising an elite event, or products which comprise plant material comprising the elite event are based on the specific genomic characteristics of the elite event, such as, a specific restriction map of the genomic region comprising the foreign DNA, molecular markers or the sequence of the flanking region(s) of the foreign DNA.

Once one or both of the flanking regions of the foreign DNA have been sequenced, primers and probes can be developed which specifically recognize this (these) sequence(s) in the nucleic acid (DNA or RNA) of a sample by way of a molecular biological technique. For instance a PCR method can be developed to identify the elite event in biological samples (such as samples of plants, plant material or products comprising plant material). Such a PCR is based on at least two specific "primers" one recognizing a sequence within the 5' or 3' flanking region of the elite event and the other recognizing a sequence within the foreign DNA. The primers preferably have a sequence of between 15 and 35 nucleotides which under optimized PCR conditions "specifically recognize" a sequence within the 5' or 3' flanking region of the elite event and the foreign DNA of the elite event respectively, so that a specific fragment ("integration fragment" or discriminating amplicon) is amplified from a nucleic acid sample comprising the elite event. This means that only the targeted integration fragment, and no other sequence in the plant genome or foreign DNA, is amplified under optimized PCR conditions.

PCR primers suitable for the invention may be the following:
  oligonucleotides ranging in length from 17 nt to about 210 nt, comprising a nucleotide sequence of at least 17 consecutive nucleotides, preferably 20 consecutive nucleotides selected from the 5' flanking sequence (SEQ ID No 1 from nucleotide 1 to nucleotide 209) at their 3' end (primers recognizing 5' flanking sequences); or
  oligonucleotides ranging in length from 17 nt to about 450 nt, comprising a nucleotide sequence of at least 17 consecutive nucleotides, preferably 20 consecutive nucleotides, selected from the 3' flanking sequence (complement of SEQ ID No 2 from nucleotide 569 to nucleotide 1000) at their 3' end (primers recognizing 3' flanking sequences); or
  oligonucleotides ranging in length from 17 nt to about 510 nt, comprising a nucleotide sequence of at least 17 consecutive nucleotides, preferably 20 nucleotides selected from the inserted DNA sequences (complement of SEQ ID No 1 from nucleotide 210 to nucleotide 720) at their 3' end (primers recognizing foreign DNA) or
  oligonucleotides ranging in length from 17 nt to about 570 nt, comprising a nucleotide sequence of at least 17 consecutive nucleotides, preferably 20 nucleotides selected from the inserted DNA sequences (SEQ ID No 2 from nucleotide 1 to nucleotide 569)

The primers may of course be longer than the mentioned 17 consecutive nucleotides, and may e.g. be 20, 21, 30, 35, 50, 75, 100, 150, 200 nt long or even longer. The primers may entirely consist of nucleotide sequence selected from the mentioned nucleotide sequences of flanking sequences and foreign DNA sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking sequences or foreign DNA, as appropriate, but may contain several (e.g. 1, 2, 5, 10 mismatches). The 5' sequence of the primers may even entirely consist of a nucleotide sequence unrelated to the flanking sequences or foreign DNA, such as e.g. a nucleotide sequence representing restriction enzyme recognition sites. Such unrelated sequences or flanking DNA sequences with mismatches should preferably be not longer than 100, more preferably not longer than 50 or even 25 nucleotides.

Moreover, suitable primers may comprise or consist of a nucleotide sequence at their 3' end spanning the joining region between the plant DNA derived sequences and the foreign DNA sequences (located at nucleotides 209-210 in SEQ ID No 1 and nucleotides 568-569 in SEQ ID No 2) provided the mentioned 3'-located 17 consecutive nucleotides are not derived exclusively from either the foreign DNA or plant-derived sequences in SEQ ID No 1 or 2.

Thus, PCR primers suitable for the invention may also be the following:
  oligonucleotides ranging in length from 17 nt to about 210 nt, comprising a nucleotide sequence of at least 17 consecutive nucleotides, preferably 20 consecutive nucleotides selected SEQ ID No 1 from nucleotide 1 to nucleotide 215) at their 3' end; or
  oligonucleotides ranging in length from 17 nt to about 450 nt, comprising a nucleotide sequence of at least 17 consecutive nucleotides, preferably 20 consecutive nucleotides, selected from the complement of SEQ ID No 2 from nucleotide 554 to nucleotide 1000) at their 3' end; or
  oligonucleotides ranging in length from 17 nt to about 510 nt, comprising a nucleotide sequence of at least 17 consecutive nucleotides, preferably 20 nucleotides selected from the complement of SEQ ID No 1 from nucleotide 195 to nucleotide 720) at their 3' end or
  oligonucleotides ranging in length from 17 nt to about 570 nt, comprising a nucleotide sequence of at least 17 consecutive nucleotides, preferably 20 nucleotides selected from SEQ ID No 2 from nucleotide 1 to nucleotide 584)

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A⇔T; G⇔C) and reading the sequence in the 5' to 3' direction, i.e. in opposite direction of the represented nucleotide sequence.

Examples of suitable primers are the oligonucleotide sequences of SEQ ID No 3, SEQ ID No 4, SEQ ID No 5 (5' flanking sequence recognizing primers) SEQ ID No 6, SEQ ID No 7, SEQ ID No 8, SEQ ID No 9, SEQ ID No 10, SEQ ID No 11 (foreign DNA recognizing primers for use with the 5' flanking sequence recognizing primers) SEQ ID No 12, SEQ ID No 13, SEQ ID No 14, SEQ ID No 15 (foreign DNA recognizing primers for use with the 3' flanking sequence recognizing primers) SEQ ID No 16, SEQ ID No 17, SEQ ID No 18 or SEQ ID No 19 (3' flanking sequence recognizing primers).

Other examples of suitable oligonucleotide primers comprise at their 3' end the following sequences or consist of such sequences:
  a. 5' flanking sequence recognizing primers:
    the nucleotide sequence of SEQ ID No 1 from nucleotide 23 to nucleotide 42
    the nucleotide sequence of SEQ ID No 1 from nucleotide 68 to nucleotide 87
    the nucleotide sequence of SEQ ID No 1 from nucleotide 69 to nucleotide 87
    the nucleotide sequence of SEQ ID No 1 from nucleotide 69 to nucleotide 88 the nucleotide sequence of SEQ ID No 1 from nucleotide 134 to nucleotide 153
the nucleotide sequence of SEQ ID No 1 from nucleotide 22 to nucleotide 42
the nucleotide sequence of SEQ ID No 1 from nucleotide 30 to nucleotide 49
the nucleotide sequence of SEQ ID No 1 from nucleotide 67 to nucleotide 87
the nucleotide sequence of SEQ ID No 1 from nucleotide 70 to nucleotide 87
the nucleotide sequence of SEQ ID No 1 from nucleotide 70 to nucleotide 88
the nucleotide sequence of SEQ ID No 1 from nucleotide 76 to nucleotide 95
the nucleotide sequence of SEQ ID No 1 from nucleotide 78 to nucleotide 97
the nucleotide sequence of SEQ ID No 1 from nucleotide 133 to nucleotide 152
the nucleotide sequence of SEQ ID No 1 from nucleotide 21 to nucleotide 42
the nucleotide sequence of SEQ ID No 1 from nucleotide 31 to nucleotide 49
the nucleotide sequence of SEQ ID No 1 from nucleotide 34 to nucleotide 63
the nucleotide sequence of SEQ ID No 1 from nucleotide 66 to nucleotide 87
the nucleotide sequence of SEQ ID No 1 from nucleotide 68 to nucleotide 88
the nucleotide sequence of SEQ ID No 1 from nucleotide 73 to nucleotide 92
the nucleotide sequence of SEQ ID No 1 from nucleotide 75 to nucleotide 95
the nucleotide sequence of SEQ ID No 1 from nucleotide 77 to nucleotide 97
the nucleotide sequence of SEQ ID No 1 from nucleotide 77 to nucleotide 95
the nucleotide sequence of SEQ ID No 1 from nucleotide 134 to nucleotide 152
the nucleotide sequence of SEQ ID No 1 from nucleotide 154 to nucleotide 173
the nucleotide sequence of SEQ ID No 1 from nucleotide 22 to nucleotide 43
the nucleotide sequence of SEQ ID No 1 from nucleotide 33 to nucleotide 53
the nucleotide sequence of SEQ ID No 1 from nucleotide 35 to nucleotide 53
the nucleotide sequence of SEQ ID No 1 from nucleotide 67 to nucleotide 88
the nucleotide sequence of SEQ ID No 1 from nucleotide 72 to nucleotide 92
the nucleotide sequence of SEQ ID No 1 from nucleotide 74 to nucleotide 92
the nucleotide sequence of SEQ ID No 1 from nucleotide 76 to nucleotide 97
the nucleotide sequence of SEQ ID No 1 from nucleotide 78 to nucleotide 95
the nucleotide sequence of SEQ ID No 1 from nucleotide 135 to nucleotide 152
the nucleotide sequence of SEQ ID No 1 from nucleotide 154 to nucleotide 171
the nucleotide sequence of SEQ ID No 1 from nucleotide 32 to nucleotide 53
the nucleotide sequence of SEQ ID No 1 from nucleotide 36 to nucleotide 57
the nucleotide sequence of SEQ ID No 1 from nucleotide 71 to nucleotide 92
the nucleotide sequence of SEQ ID No 1 from nucleotide 74 to nucleotide 95
the nucleotide sequence of SEQ ID No 1 from nucleotide 75 to nucleotide 92
the nucleotide sequence of SEQ ID No 1 from nucleotide 32 to nucleotide 51
the nucleotide sequence of SEQ ID No 1 from nucleotide 31 to nucleotide 51
the nucleotide sequence of SEQ ID No 1 from nucleotide 33 to nucleotide 51
the nucleotide sequence of SEQ ID No 1 from nucleotide 30 to nucleotide 51
the nucleotide sequence of SEQ ID No 1 from nucleotide 34 to nucleotide 51
the nucleotide sequence of SEQ ID No 1 from nucleotide 205 to nucleotide 226 b. foreign DNA sequence recognizing primers for use with 5' flanking sequence recognizing primers:

the complement of the nucleotide sequence of SEQ ID No 1 from nucleotide 201 to nucleotide 220
the complement of the nucleotide sequence of SEQ ID No 1 from nucleotide 220 to nucleotide 239
the complement of the nucleotide sequence of SEQ ID No 1 from nucleotide 361 to nucleotide 380
the complement of the nucleotide sequence of SEQ ID No 1 from nucleotide 366 to nucleotide 385
the complement of the nucleotide sequence of SEQ ID No 1 from nucleotide 201 to nucleotide 219
the complement of the nucleotide sequence of SEQ ID No 1 from nucleotide 220 to nucleotide 238
the complement of the nucleotide sequence of SEQ ID No 1 from nucleotide 221 to nucleotide 239
the complement of the nucleotide sequence of SEQ ID No 1 from nucleotide 358 to nucleotide 377
the complement of the nucleotide sequence of SEQ ID No 1 from nucleotide 359 to nucleotide 378
the complement of the nucleotide sequence of SEQ ID No 1 from nucleotide 361 to nucleotide 379
the complement of the nucleotide sequence of SEQ ID No 1 from nucleotide 366 to nucleotide 384
the complement of the nucleotide sequence of SEQ ID No 1 from nucleotide 368 to nucleotide 387
the complement of the nucleotide sequence of SEQ ID No 1 from nucleotide 496 to nucleotide 515
the complement of the nucleotide sequence of SEQ ID No 1 from nucleotide 656 to nucleotide 675
the complement of the nucleotide sequence of SEQ ID No 1 from nucleotide 201 to nucleotide 218
the complement of the nucleotide sequence of SEQ ID No 1 from nucleotide 220 to nucleotide 237
the complement of the nucleotide sequence of SEQ ID No 1 from nucleotide 221 to nucleotide 238
the complement of the nucleotide sequence of SEQ ID No 1 from nucleotide 220 to nucleotide 240
the complement of the nucleotide sequence of SEQ ID No 1 from nucleotide 221 to nucleotide 240
the complement of the nucleotide sequence of SEQ ID No 1 from nucleotide 251 to nucleotide 270
the complement of the nucleotide sequence of SEQ ID No 1 from nucleotide 252 to nucleotide 271
the complement of the nucleotide sequence of SEQ ID No 1 from nucleotide 253 to nucleotide 272
the complement of the nucleotide sequence of SEQ ID No 1 from nucleotide 359 to nucleotide 377
the complement of the nucleotide sequence of SEQ ID No 1 from nucleotide 361 to nucleotide 378 the complement of the nucleotide sequence of SEQ ID No 1 from nucleotide 358 to nucleotide 378
the complement of the nucleotide sequence of SEQ ID No 1 from nucleotide 359 to nucleotide 379
the complement of the nucleotide sequence of SEQ ID No 1 from nucleotide 361 to nucleotide 382
the complement of the nucleotide sequence of SEQ ID No 1 from nucleotide 366 to nucleotide 383
the complement of the nucleotide sequence of SEQ ID No 1 from nucleotide 368 to nucleotide 386
the complement of the nucleotide sequence of SEQ ID No 1 from nucleotide 366 to nucleotide 386
the complement of the nucleotide sequence of SEQ ID No 1 from nucleotide 375 to nucleotide 393
the complement of the nucleotide sequence of SEQ ID No 1 from nucleotide 375 to nucleotide 394
the complement of the nucleotide sequence of SEQ ID No 1 from nucleotide 496 to nucleotide 514
the complement of the nucleotide sequence of SEQ ID No 1 from nucleotide 498 to nucleotide 515
the complement of the nucleotide sequence of SEQ ID No 1 from nucleotide 562 to nucleotide 581
the complement of the nucleotide sequence of SEQ ID No 1 from nucleotide 608 to nucleotide 627
the complement of the nucleotide sequence of SEQ ID No 1 from nucleotide 651 to nucleotide 670
the complement of the nucleotide sequence of SEQ ID No 1 from nucleotide 655 to nucleotide 674
the complement of the nucleotide sequence of SEQ ID No 1 from nucleotide 656 to nucleotide 674
the complement of the nucleotide sequence of SEQ ID No 1 from nucleotide 656 to nucleotide 676
the complement of the nucleotide sequence of SEQ ID No 1 from nucleotide 669 to nucleotide 678
the complement of the nucleotide sequence of SEQ ID No 1 from nucleotide 252 to nucleotide 270
the complement of the nucleotide sequence of SEQ ID No 1 from nucleotide 253 to nucleotide 271
the complement of the nucleotide sequence of SEQ ID No 1 from nucleotide 251 to nucleotide 271
the complement of the nucleotide sequence of SEQ ID No 1 from nucleotide 252 to nucleotide 272
the complement of the nucleotide sequence of SEQ ID No 1 from nucleotide 267 to nucleotide 286
the complement of the nucleotide sequence of SEQ ID No 1 from nucleotide 359 to nucleotide 376
the complement of the nucleotide sequence of SEQ ID No 1 from nucleotide 358 to nucleotide 379
the complement of the nucleotide sequence of SEQ ID No 1 from nucleotide 362 to nucleotide 379
the complement of the nucleotide sequence of SEQ ID No 1 from nucleotide 359 to nucleotide 380
the complement of the nucleotide sequence of SEQ ID No 1 from nucleotide 368 to nucleotide 385
the complement of the nucleotide sequence of SEQ ID No 1 from nucleotide 368 to nucleotide 388
the complement of the nucleotide sequence of SEQ ID No 1 from nucleotide 375 to nucleotide 392
the complement of the nucleotide sequence of SEQ ID No 1 from nucleotide 376 to nucleotide 393
the complement of the nucleotide sequence of SEQ ID No 1 from nucleotide 376 to nucleotide 394
the complement of the nucleotide sequence of SEQ ID No 1 from nucleotide 376 to nucleotide 395
the complement of the nucleotide sequence of SEQ ID No 1 from nucleotide 440 to nucleotide 459
the complement of the nucleotide sequence of SEQ ID No 1 from nucleotide 442 to nucleotide 461
the complement of the nucleotide sequence of SEQ ID No 1 from nucleotide 496 to nucleotide 513
the complement of the nucleotide sequence of SEQ ID No 1 from nucleotide 556 to nucleotide 575
the complement of the nucleotide sequence of SEQ ID No 1 from nucleotide 558 to nucleotide 577
the complement of the nucleotide sequence of SEQ ID No 1 from nucleotide 561 to nucleotide 580
the complement of the nucleotide sequence of SEQ ID No 1 from nucleotide 563 to nucleotide 582
the complement of the nucleotide sequence of SEQ ID No 1 from nucleotide 562 to nucleotide 582
the complement of the nucleotide sequence of SEQ ID No 1 from nucleotide 608 to nucleotide 628
the complement of the nucleotide sequence of SEQ ID No 1 from nucleotide 637 to nucleotide 656
the complement of the nucleotide sequence of SEQ ID No 1 from nucleotide 644 to nucleotide 663
the complement of the nucleotide sequence of SEQ ID No 1 from nucleotide 651 to nucleotide 669
the complement of the nucleotide sequence of SEQ ID No 1 from nucleotide 651 to nucleotide 671
the complement of the nucleotide sequence of SEQ ID No 1 from nucleotide 656 to nucleotide 673
the complement of the nucleotide sequence of SEQ ID No 1 from nucleotide 655 to nucleotide 675
the complement of the nucleotide sequence of SEQ ID No 1 from nucleotide 659 to nucleotide 677
the complement of the nucleotide sequence of SEQ ID No 1 from nucleotide 659 to nucleotide 679
the complement of the nucleotide sequence of SEQ ID No 1 from nucleotide 201 to nucleotide 222
the complement of the nucleotide sequence of SEQ ID No 1 from nucleotide 204 to nucleotide 225
the complement of the nucleotide sequence of SEQ ID No 1 from nucleotide 223 to nucleotide 240
the complement of the nucleotide sequence of SEQ ID No 1 from nucleotide 223 to nucleotide 241
the complement of the nucleotide sequence of SEQ ID No 1 from nucleotide 220 to nucleotide 241
the complement of the nucleotide sequence of SEQ ID No 1 from nucleotide 221 to nucleotide 241
the complement of the nucleotide sequence of SEQ ID No 1 from nucleotide 253 to nucleotide 270
the complement of the nucleotide sequence of SEQ ID No 1 from nucleotide 251 to nucleotide 272
the complement of the nucleotide sequence of SEQ ID No 1 from nucleotide 252 to nucleotide 273
the complement of the nucleotide sequence of SEQ ID No 1 from nucleotide 253 to nucleotide 274
the complement of the nucleotide sequence of SEQ ID No 1 from nucleotide 268 to nucleotide 289
the complement of the nucleotide sequence of SEQ ID No 1 from nucleotide 377 to nucleotide 394
the complement of the nucleotide sequence of SEQ ID No 1 from nucleotide 375 to nucleotide 395
the complement of the nucleotide sequence of SEQ ID No 1 from nucleotide 440 to nucleotide 458
the complement of the nucleotide sequence of SEQ ID No 1 from nucleotide 442 to nucleotide 460
the complement of the nucleotide sequence of SEQ ID No 1 from nucleotide 440 to nucleotide 460
the complement of the nucleotide sequence of SEQ ID No 1 from nucleotide 442 to nucleotide 462 the complement of the nucleotide sequence of SEQ ID No 1 from nucleotide 492 to nucleotide 513
the complement of the nucleotide sequence of SEQ ID No 1 from nucleotide 503 to nucleotide 522
the complement of the nucleotide sequence of SEQ ID No 1 from nucleotide 556 to nucleotide 574
the complement of the nucleotide sequence of SEQ ID No 1 from nucleotide 556 to nucleotide 576
the complement of the nucleotide sequence of SEQ ID No 1 from nucleotide 562 to nucleotide 579
the complement of the nucleotide sequence of SEQ ID No 1 from nucleotide 563 to nucleotide 581
the complement of the nucleotide sequence of SEQ ID No 1 from nucleotide 563 to nucleotide 583
the complement of the nucleotide sequence of SEQ ID No 1 from nucleotide 562 to nucleotide 583
the complement of the nucleotide sequence of SEQ ID No 1 from nucleotide 608 to nucleotide 625
the complement of the nucleotide sequence of SEQ ID No 1 from nucleotide 608 to nucleotide 629
the complement of the nucleotide sequence of SEQ ID No 1 from nucleotide 644 to nucleotide 662
the complement of the nucleotide sequence of SEQ ID No 1 from nucleotide 651 to nucleotide 668
the complement of the nucleotide sequence of SEQ ID No 1 from nucleotide 651 to nucleotide 672
the complement of the nucleotide sequence of SEQ ID No 1 from nucleotide 655 to nucleotide 676
the complement of the nucleotide sequence of SEQ ID No 1 from nucleotide 655 to nucleotide 677
the complement of the nucleotide sequence of SEQ ID No 1 from nucleotide 659 to nucleotide 680
the complement of the nucleotide sequence of SEQ ID No 1 from nucleotide 657 to nucleotide 688
the complement of the nucleotide sequence of SEQ ID No 1 from nucleotide 223 to nucleotide 242
the complement of the nucleotide sequence of SEQ ID No 1 from nucleotide 267 to nucleotide 288
the complement of the nucleotide sequence of SEQ ID No 1 from nucleotide 368 to nucleotide 389
the complement of the nucleotide sequence of SEQ ID No 1 from nucleotide 375 to nucleotide 396
the complement of the nucleotide sequence of SEQ ID No 1 from nucleotide 376 to nucleotide 397
the complement of the nucleotide sequence of SEQ ID No 1 from nucleotide 440 to nucleotide 457
the complement of the nucleotide sequence of SEQ ID No 1 from nucleotide 442 to nucleotide 459
the complement of the nucleotide sequence of SEQ ID No 1 from nucleotide 442 to nucleotide 463
the complement of the nucleotide sequence of SEQ ID No 1 from nucleotide 534 to nucleotide 553
the complement of the nucleotide sequence of SEQ ID No 1 from nucleotide 558 to nucleotide 575
the complement of the nucleotide sequence of SEQ ID No 1 from nucleotide 556 to nucleotide 577
the complement of the nucleotide sequence of SEQ ID No 1 from nucleotide 563 to nucleotide 580
the complement of the nucleotide sequence of SEQ ID No 1 from nucleotide 563 to nucleotide 584
the complement of the nucleotide sequence of SEQ ID No 1 from nucleotide 644 to nucleotide 661
the complement of the nucleotide sequence of SEQ ID No 1 from nucleotide 645 to nucleotide 662
the complement of the nucleotide sequence of SEQ ID No 1 from nucleotide 644 to nucleotide 665
the complement of the nucleotide sequence of SEQ ID No 1 from nucleotide 645 to nucleotide 666
the complement of the nucleotide sequence of SEQ ID No 1 from nucleotide 325 to nucleotide 342
the complement of the nucleotide sequence of SEQ ID No 1 from nucleotide 503 to nucleotide 520
the complement of the nucleotide sequence of SEQ ID No 1 from nucleotide 534 to nucleotide 554
the complement of the nucleotide sequence of SEQ ID No 1 from nucleotide 221 to nucleotide 242
the complement of the nucleotide sequence of SEQ ID No 1 from nucleotide 505 to nucleotide 522
the complement of the nucleotide sequence of SEQ ID No 1 from nucleotide 534 to nucleotide 551
the complement of the nucleotide sequence of SEQ ID No 1 from nucleotide 534 to nucleotide 555
the complement of the nucleotide sequence of SEQ ID No 1 from nucleotide 536 to nucleotide 557
the complement of the nucleotide sequence of SEQ ID No 1 from nucleotide 551 to nucleotide 570
the complement of the nucleotide sequence of SEQ ID No 1 from nucleotide 551 to nucleotide 571
the complement of the nucleotide sequence of SEQ ID No 1 from nucleotide 551 to nucleotide 572 c. foreign DNA sequence recognizing primers for use with 3' flanking sequence recognizing primers:
the complement of the nucleotide sequence of SEQ ID No 2 from nucleotide 955 to nucleotide 974
the complement of the nucleotide sequence of SEQ ID No 2 from nucleotide 955 to nucleotide 973
the complement of the nucleotide sequence of SEQ ID No 2 from nucleotide 955 to nucleotide 972
the complement of the nucleotide sequence of SEQ ID No 2 from nucleotide 958 to nucleotide 975
the complement of the nucleotide sequence of SEQ ID No 2 from nucleotide 958 to nucleotide 977
the complement of the nucleotide sequence of SEQ ID No 2 from nucleotide 917 to nucleotide 934
the complement of the nucleotide sequence of SEQ ID No 2 from nucleotide 947 to nucleotide 968
the complement of the nucleotide sequence of SEQ ID No 2 from nucleotide 951 to nucleotide 968
the complement of the nucleotide sequence of SEQ ID No 2 from nucleotide 951 to nucleotide 972
the complement of the nucleotide sequence of SEQ ID No 2 from nucleotide 958 to nucleotide 976
the complement of the nucleotide sequence of SEQ ID No 2 from nucleotide 955 to nucleotide 976
the complement of the nucleotide sequence of SEQ ID No 2 from nucleotide 958 to nucleotide 979 d. 3' flanking sequence recognizing primers:
the nucleotide sequence of SEQ ID No 2 from nucleotide 151 to nucleotide 170
the nucleotide sequence of SEQ ID No 2 from nucleotide 152 to nucleotide 171
the nucleotide sequence of SEQ ID No 2 from nucleotide 6 to nucleotide 25
the nucleotide sequence of SEQ ID No 2 from nucleotide 148 to nucleotide 167
the nucleotide sequence of SEQ ID No 2 from nucleotide 151 to nucleotide 171
the nucleotide sequence of SEQ ID No 2 from nucleotide 152 to nucleotide 170
the nucleotide sequence of SEQ ID No 2 from nucleotide 153 to nucleotide 171
the nucleotide sequence of SEQ ID No 2 from nucleotide 5 to nucleotide 25 the nucleotide sequence of SEQ ID No 2 from nucleotide 7 to nucleotide 25
the nucleotide sequence of SEQ ID No 2 from nucleotide 67 to nucleotide 86
the nucleotide sequence of SEQ ID No 2 from nucleotide 89 to nucleotide 108
the nucleotide sequence of SEQ ID No 2 from nucleotide 134 to nucleotide 153
the nucleotide sequence of SEQ ID No 2 from nucleotide 147 to nucleotide 167
the nucleotide sequence of SEQ ID No 2 from nucleotide 150 to nucleotide 171
the nucleotide sequence of SEQ ID No 2 from nucleotide 153 to nucleotide 170
the nucleotide sequence of SEQ ID No 2 from nucleotide 154 to nucleotide 171
the nucleotide sequence of SEQ ID No 2 from nucleotide 168 to nucleotide 187
the nucleotide sequence of SEQ ID No 2 from nucleotide 169 to nucleotide 187
the nucleotide sequence of SEQ ID No 2 from nucleotide 171 to nucleotide 190
the nucleotide sequence of SEQ ID No 2 from nucleotide 197 to nucleotide 216
the nucleotide sequence of SEQ ID No 2 from nucleotide 236 to nucleotide 255
the nucleotide sequence of SEQ ID No 2 from nucleotide 280 to nucleotide 299
the nucleotide sequence of SEQ ID No 2 from nucleotide 4 to nucleotide 25
the nucleotide sequence of SEQ ID No 2 from nucleotide 8 to nucleotide 25
the nucleotide sequence of SEQ ID No 2 from nucleotide 63 to nucleotide 82
the nucleotide sequence of SEQ ID No 2 from nucleotide 66 to nucleotide 86
the nucleotide sequence of SEQ ID No 2 from nucleotide 68 to nucleotide 87
the nucleotide sequence of SEQ ID No 2 from nucleotide 90 to nucleotide 108
the nucleotide sequence of SEQ ID No 2 from nucleotide 93 to nucleotide 112
the nucleotide sequence of SEQ ID No 2 from nucleotide 94 to nucleotide 113
the nucleotide sequence of SEQ ID No 2 from nucleotide 96 to nucleotide 115
the nucleotide sequence of SEQ ID No 2 from nucleotide 101 to nucleotide 120
the nucleotide sequence of SEQ ID No 2 from nucleotide 134 to nucleotide 154
the nucleotide sequence of SEQ ID No 2 from nucleotide 146 to nucleotide 167
the nucleotide sequence of SEQ ID No 2 from nucleotide 150 to nucleotide 167
the nucleotide sequence of SEQ ID No 2 from nucleotide 170 to nucleotide 190
the nucleotide sequence of SEQ ID No 2 from nucleotide 172 to nucleotide 190
the nucleotide sequence of SEQ ID No 2 from nucleotide 186 to nucleotide 205
the nucleotide sequence of SEQ ID No 2 from nucleotide 189 to nucleotide 208
the nucleotide sequence of SEQ ID No 2 from nucleotide 190 to nucleotide 209
the nucleotide sequence of SEQ ID No 2 from nucleotide 191 to nucleotide 210
the nucleotide sequence of SEQ ID No 2 from nucleotide 195 to nucleotide 214
the nucleotide sequence of SEQ ID No 2 from nucleotide 196 to nucleotide 216
the nucleotide sequence of SEQ ID No 2 from nucleotide 196 to nucleotide 214
the nucleotide sequence of SEQ ID No 2 from nucleotide 198 to nucleotide 216
the nucleotide sequence of SEQ ID No 2 from nucleotide 199 to nucleotide 216
the nucleotide sequence of SEQ ID No 2 from nucleotide 208 to nucleotide 227
the nucleotide sequence of SEQ ID No 2 from nucleotide 234 to nucleotide 253
the nucleotide sequence of SEQ ID No 2 from nucleotide 235 to nucleotide 255
the nucleotide sequence of SEQ ID No 2 from nucleotide 279 to nucleotide 299
the nucleotide sequence of SEQ ID No 2 from nucleotide 281 to nucleotide 299
the nucleotide sequence of SEQ ID No 2 from nucleotide 285 to nucleotide 304
the nucleotide sequence of SEQ ID No 2 from nucleotide 296 to nucleotide 315
the nucleotide sequence of SEQ ID No 2 from nucleotide 396 to nucleotide 415
the nucleotide sequence of SEQ ID No 2 from nucleotide 64 to nucleotide 82
the nucleotide sequence of SEQ ID No 2 from nucleotide 65 to nucleotide 86
the nucleotide sequence of SEQ ID No 2 from nucleotide 67 to nucleotide 87
the nucleotide sequence of SEQ ID No 2 from nucleotide 75 to nucleotide 92
the nucleotide sequence of SEQ ID No 2 from nucleotide 91 to nucleotide 108
the nucleotide sequence of SEQ ID No 2 from nucleotide 92 to nucleotide 112
the nucleotide sequence of SEQ ID No 2 from nucleotide 93 to nucleotide 113
the nucleotide sequence of SEQ ID No 2 from nucleotide 94 to nucleotide 112
the nucleotide sequence of SEQ ID No 2 from nucleotide 95 to nucleotide 115
the nucleotide sequence of SEQ ID No 2 from nucleotide 95 to nucleotide 113
the nucleotide sequence of SEQ ID No 2 from nucleotide 97 to nucleotide 115
the nucleotide sequence of SEQ ID No 2 from nucleotide 100 to nucleotide 120
the nucleotide sequence of SEQ ID No 2 from nucleotide 132 to nucleotide 153
the nucleotide sequence of SEQ ID No 2 from nucleotide 133 to nucleotide 154
the nucleotide sequence of SEQ ID No 2 from nucleotide 163 to nucleotide 182
the nucleotide sequence of SEQ ID No 2 from nucleotide 165 to nucleotide 184
the nucleotide sequence of SEQ ID No 2 from nucleotide 167 to nucleotide 187
the nucleotide sequence of SEQ ID No 2 from nucleotide 169 to nucleotide 190
the nucleotide sequence of SEQ ID No 2 from nucleotide 173 to nucleotide 190
the nucleotide sequence of SEQ ID No 2 from nucleotide 187 to nucleotide 205 the nucleotide sequence of SEQ ID No 2 from nucleotide 189 to nucleotide 209
the nucleotide sequence of SEQ ID No 2 from nucleotide 190 to nucleotide 210
the nucleotide sequence of SEQ ID No 2 from nucleotide 190 to nucleotide 208
the nucleotide sequence of SEQ ID No 2 from nucleotide 191 to nucleotide 209
the nucleotide sequence of SEQ ID No 2 from nucleotide 192 to nucleotide 210
the nucleotide sequence of SEQ ID No 2 from nucleotide 194 to nucleotide 214
the nucleotide sequence of SEQ ID No 2 from nucleotide 197 to nucleotide 214
the nucleotide sequence of SEQ ID No 2 from nucleotide 233 to nucleotide 253
the nucleotide sequence of SEQ ID No 2 from nucleotide 234 to nucleotide 255
the nucleotide sequence of SEQ ID No 2 from nucleotide 235 to nucleotide 253
the nucleotide sequence of SEQ ID No 2 from nucleotide 282 to nucleotide 299
the nucleotide sequence of SEQ ID No 2 from nucleotide 295 to nucleotide 315
the nucleotide sequence of SEQ ID No 2 from nucleotide 297 to nucleotide 315
the nucleotide sequence of SEQ ID No 2 from nucleotide 397 to nucleotide 415
the nucleotide sequence of SEQ ID No 2 from nucleotide 65 to nucleotide 82
the nucleotide sequence of SEQ ID No 2 from nucleotide 66 to nucleotide 87
the nucleotide sequence of SEQ ID No 2 from nucleotide 75 to nucleotide 96
the nucleotide sequence of SEQ ID No 2 from nucleotide 91 to nucleotide 112
the nucleotide sequence of SEQ ID No 2 from nucleotide 92 to nucleotide 112
the nucleotide sequence of SEQ ID No 2 from nucleotide 94 to nucleotide 115
the nucleotide sequence of SEQ ID No 2 from nucleotide 95 to nucleotide 112
the nucleotide sequence of SEQ ID No 2 from nucleotide 98 to nucleotide 115
the nucleotide sequence of SEQ ID No 2 from nucleotide 99 to nucleotide 120
the nucleotide sequence of SEQ ID No 2 from nucleotide 162 to nucleotide 182
the nucleotide sequence of SEQ ID No 2 from nucleotide 164 to nucleotide 182
the nucleotide sequence of SEQ ID No 2 from nucleotide 164 to nucleotide 184
the nucleotide sequence of SEQ ID No 2 from nucleotide 164 to nucleotide 184
the nucleotide sequence of SEQ ID No 2 from nucleotide 184 to nucleotide 205
the nucleotide sequence of SEQ ID No 2 from nucleotide 187 to nucleotide 208
the nucleotide sequence of SEQ ID No 2 from nucleotide 188 to nucleotide 205
the nucleotide sequence of SEQ ID No 2 from nucleotide 188 to nucleotide 209
the nucleotide sequence of SEQ ID No 2 from nucleotide 189 to nucleotide 210
the nucleotide sequence of SEQ ID No 2 from nucleotide 191 to nucleotide 208
the nucleotide sequence of SEQ ID No 2 from nucleotide 192 to nucleotide 209
the nucleotide sequence of SEQ ID No 2 from nucleotide 193 to nucleotide 214
the nucleotide sequence of SEQ ID No 2 from nucleotide 205 to nucleotide 212
the nucleotide sequence of SEQ ID No 2 from nucleotide 232 to nucleotide 253
the nucleotide sequence of SEQ ID No 2 from nucleotide 236 to nucleotide 253
the nucleotide sequence of SEQ ID No 2 from nucleotide 242 to nucleotide 261
the nucleotide sequence of SEQ ID No 2 from nucleotide 278 to nucleotide 299
the nucleotide sequence of SEQ ID No 2 from nucleotide 283 to nucleotide 304
the nucleotide sequence of SEQ ID No 2 from nucleotide 287 to nucleotide 304
the nucleotide sequence of SEQ ID No 2 from nucleotide 294 to nucleotide 315
the nucleotide sequence of SEQ ID No 2 from nucleotide 298 to nucleotide 315
the nucleotide sequence of SEQ ID No 2 from nucleotide 332 to nucleotide 349
the nucleotide sequence of SEQ ID No 2 from nucleotide 398 to nucleotide 415
the nucleotide sequence of SEQ ID No 2 from nucleotide 161 to nucleotide 182
the nucleotide sequence of SEQ ID No 2 from nucleotide 163 to nucleotide 184
the nucleotide sequence of SEQ ID No 2 from nucleotide 165 to nucleotide 182
the nucleotide sequence of SEQ ID No 2 from nucleotide 166 to nucleotide 187
the nucleotide sequence of SEQ ID No 2 from nucleotide 241 to nucleotide 261
the nucleotide sequence of SEQ ID No 2 from nucleotide 243 to nucleotide 261
the nucleotide sequence of SEQ ID No 2 from nucleotide 244 to nucleotide 261
the nucleotide sequence of SEQ ID No 2 from nucleotide 240 to nucleotide 261
the nucleotide sequence of SEQ ID No 2 from nucleotide 126 to nucleotide 145
the nucleotide sequence of SEQ ID No 2 from nucleotide 208 to nucleotide 225
the nucleotide sequence of SEQ ID No 2 from nucleotide 124 to nucleotide 145
the nucleotide sequence of SEQ ID No 2 from nucleotide 75 to nucleotide 94
the nucleotide sequence of SEQ ID No 2 from nucleotide 231 to nucleotide 250
the nucleotide sequence of SEQ ID No 2 from nucleotide 243 to nucleotide 262
the nucleotide sequence of SEQ ID No 2 from nucleotide 230 to nucleotide 250
the nucleotide sequence of SEQ ID No 2 from nucleotide 232 to nucleotide 250
the nucleotide sequence of SEQ ID No 2 from nucleotide 242 to nucleotide 262
the nucleotide sequence of SEQ ID No 2 from nucleotide 244 to nucleotide 262
the nucleotide sequence of SEQ ID No 2 from nucleotide 229 to nucleotide 250
the nucleotide sequence of SEQ ID No 2 from nucleotide 241 to nucleotide 262 the nucleotide sequence of SEQ ID No 2 from nucleotide 245 to nucleotide 262
the nucleotide sequence of SEQ ID No 2 from nucleotide 287 to nucleotide 306
the nucleotide sequence of SEQ ID No 2 from nucleotide 288 to nucleotide 306
the nucleotide sequence of SEQ ID No 2 from nucleotide 230 to nucleotide 247
the nucleotide sequence of SEQ ID No 2 from nucleotide 285 to nucleotide 306
the nucleotide sequence of SEQ ID No 2 from nucleotide 289 to nucleotide 306
the nucleotide sequence of SEQ ID No 2 from nucleotide 282 to nucleotide 303
the nucleotide sequence of SEQ ID No 2 from nucleotide 288 to nucleotide 307
the nucleotide sequence of SEQ ID No 2 from nucleotide 287 to nucleotide 307
the nucleotide sequence of SEQ ID No 2 from nucleotide 289 to nucleotide 307
the nucleotide sequence of SEQ ID No 2 from nucleotide 286 to nucleotide 307
the nucleotide sequence of SEQ ID No 2 from nucleotide 290 to nucleotide 307
the nucleotide sequence of SEQ ID No 2 from nucleotide 229 to nucleotide 248
the nucleotide sequence of SEQ ID No 2 from nucleotide 230 to nucleotide 248
the nucleotide sequence of SEQ ID No 2 from nucleotide 227 to nucleotide 248
the nucleotide sequence of SEQ ID No 2 from nucleotide 231 to nucleotide 248

As used herein, "the nucleotide sequence of SEQ ID No. Z from position X to position Y" indicates the nucleotide sequence including both nucleotide endpoints.

Preferably, the integration fragment has a length of between 50 and 500 nucleotides, most preferably of between 100 and 350 nucleotides. The specific primers may have a sequence which is between 80 and 100% identical to a sequence within the 5' or 3' flanking region of the elite event and the foreign DNA of the elite event, respectively, provided the mismatches still allow specific identification of the elite event with these primers under optimized PCR conditions. The range of allowable mismatches however, can easily be determined experimentally and are known to a person skilled in the art.

The following table exemplifies the sizes of expected DNA amplicons (or integration fragments) with selected pairs of PCR primers.

| Primer 1 | From position | Primer 2 | To position | Length amplicon |
|---|---|---|---|---|
| HCA148 | 12 | KVM174 | 225 | 213 |
| HCA148 | 12 | KVM177 | 253 | 241 |
| HCA148 | 12 | DPA024 | 316 | 304 |
| HCA148 | 12 | MDB390 | 396 | 384 |
| HCA148 | 12 | HCA023 | 511 | 499 |
| HCA148 | 12 | DPA007 | 634 | 622 |
| DPA021 | 134 | KVM174 | 225 | 91 |
| DPA021 | 134 | KVM177 | 253 | 119 |
| DPA021 | 134 | DPA024 | 316 | 182 |
| DPA021 | 134 | MDB390 | 396 | 262 |
| DPA021 | 134 | HCA023 | 511 | 377 |
| DPA021 | 134 | DPA007 | 634 | 500 |
| KVM176 | 187 | KVM174 | 225 | 38 |
| KVM176 | 187 | KVM177 | 253 | 66 |
| KVM176 | 187 | DPA024 | 316 | 129 |

-continued

| Primer 1 | From position | Primer 2 | To position | Length amplicon |
|---|---|---|---|---|
| KVM176 | 187 | MDB390 | 396 | 209 |
| KVM176 | 187 | HCA023 | 511 | 324 |
| KVM176 | 187 | DPA007 | 634 | 447 |
| YTP007 | 116 | HCA074 | 628 | 512 |
| YTP007 | 116 | SMO017 | 667 | 551 |
| YTP007 | 116 | SMO027 | 710 | 594 |
| YTP007 | 116 | SMO033 | 867 | 751 |
| MDB452 | 187 | HCA074 | 628 | 441 |
| MDB452 | 187 | SMO017 | 667 | 480 |
| MDB452 | 187 | SMO027 | 710 | 523 |
| MDB452 | 187 | SMO033 | 867 | 680 |
| HCA014 | 398 | HCA074 | 628 | 230 |
| HCA014 | 398 | SMO017 | 667 | 269 |
| HCA014 | 398 | SMO027 | 710 | 312 |
| HCA014 | 398 | SMO033 | 867 | 469 |
| MDB402 | 528 | HCA074 | 628 | 100 |
| MDB402 | 528 | SMO017 | 667 | 139 |
| MDB402 | 528 | SMO027 | 710 | 182 |
| MDB402 | 528 | SMO033 | 867 | 339 |

Detection of integration fragments can occur in various ways e.g. via size estimation after gel analysis. The integration fragments may also be directly sequenced. Other sequence specific methods for detection of amplified DNA fragments are also known in the art.

As the sequence of the primers and their relative location in the genome are unique for the elite event, amplification of the integration fragment will occur only in biological samples comprising (the nucleic acid of) the elite event. Preferably when performing a PCR to identify the presence of A2704-12 in unknown samples, a control is included of a set of primers with which a fragment within a "housekeeping gene" of the plant species of the event can be amplified. Housekeeping genes are genes that are expressed in most cell types and which are concerned with basic metabolic activities common to all cells. Preferably, the fragment amplified from the housekeeping gene is a fragment which is larger than the amplified integration fragment. Depending on the samples to be analyzed, other controls can be included.

Standard PCR protocols are described in the art, such as in "PCR Applications Manual" (Roche Molecular Biochemicals, 2nd Edition, 1999). The optimal conditions for the PCR, including the sequence of the specific primers, is specified in a "PCR identification protocol" for each elite event. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Alternatively, specific primers can be used to amplify an integration fragment that can be used as a "specific probe" for identifying A2704-12 in biological samples. Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of A2704-12. Such identification methods based on hybridization with a specific probe (either on a solid phase carrier or in solution) have been described in the art. The specific probe is preferably a sequence which, under optimized conditions, hybridizes specifically to a region within the 5' or 3' flanking region of the elite event and preferably also comprising part of the foreign DNA contiguous therewith (hereinafter referred to as "specific region"). Preferably, the specific probe comprises a sequence of between 50 and 500 bp, preferably of 100 to 350 bp which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 15 to about 100 contiguous nucleotides identical (or complementary) to a specific region of the elite event.

A "kit" as used herein refers to a set of reagents for the purpose of performing the method of the invention, more particularly, the identification of the elite event A2704-12 in biological samples. More particularly, a preferred embodiment of the kit of the invention comprises at least one or two specific primers, as described above. Optionally, the kit can further comprise any other reagent described herein in the PCR identification protocol. Alternatively, according to another embodiment of this invention, the kit can comprise a specific probe, as described above, which specifically hybridizes with nucleic acid of biological samples to identify the presence of A2704-12 therein. Optionally, the kit can further comprise any other reagent (such as but not limited to hybridizing buffer, label) for identification of A2704-12 in biological samples, using the specific probe.

The kit of the invention can be used, and its components can be specifically adjusted, for purposes of quality control (e.g., purity of seed lots), detection of the elite event in plant material or material comprising or derived from plant material, such as but not limited to food or feed products.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983, Proc. Nat. Acad. Sci. USA 80:726) using a window-size of 20 nucleotides, a word length of 4 nucleotides, and a gap penalty of 4. Computer-assisted analysis and interpretation of sequence data, including sequence alignment as described above, can, e.g., be conveniently performed using the programs of the Intelligenetics™ Suite (Intelligenetics Inc., CA) or the sequence analysis software package of the Genetics Computer Group (GCG, University of Wisconsin Biotechnology center). Sequences are indicated as "essentially similar" when such sequences have a sequence identity of at least about 75%, particularly at least about 80%, more particularly at least about 85%, quite particularly about 90%, especially about 95%, more especially about 100%. It is clear than when RNA sequences are said to be essentially similar or have a certain degree of sequence identity with DNA sequences, thymidine (T) in the DNA sequence is considered equal to uracil (U) in the RNA sequence.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in the elite event under the conditions set forth in the method (such as the conditions of the PCR identification protocol), whereby the specificity is determined by the presence of positive and negative controls.

The term "hybridizing" as used herein when referring to specific probes, refer to the fact that the probe binds to a specific region in the nucleic acid sequence of the elite event under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2×SSC, 0.1% SDS, and 7) exposing the filter for 24 to 48 hours to X-ray film at −70° C. with an intensifying screen.

As used in herein, a biological samples is a sample of a plant, plant material or products comprising plant material. The term "plant" is intended to encompass soybean (*Glycine max*) plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the present invention, such biological samples are tested for the presence of nucleic acids specific for A2704-12, implying the presence of nucleic acids in the samples. Thus the methods referred to herein for identifying elite event A2704-12 in biological samples, relate to the identification in biological samples of nucleic acids which comprise the elite event.

As used herein "comprising" is to be interpreted as specifying the presence of the stated features, integers, steps, reagents or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, etc.

The present invention also relates to the development of an elite event A2704-12 in soybean to the plants comprising this event, the progeny obtained from these plants and to the plant cells, or plant material derived from this event. Plants comprising elite event A2704-12 were obtained through as described in example 1.

Soybean plants or plant material comprising A2704-12 can be identified according to the PCR identification protocol described for A2704-12 in Example 2. Briefly, soybean genomic DNA present in the biological sample is amplified by PCR using a primer which specifically recognizes a sequence within the 5' or 3' flanking sequence of A2704-12 such as the primer with the sequence of SEQ ID NO: 4, and a primer which recognizes a sequence in the foreign DNA, such as the primer with the sequence of SEQ ID NO: 8. DNA primers which amplify part of an endogenous soybean sequence are used as positive control for the PCR amplification. If upon PCR amplification, the material yields a fragment of the expected size, the material contains plant material from a soybean plant harboring elite event A2704-12.

Plants harboring A2704-12 are characterized by their glufosinate tolerance, which in the context of the present invention includes that plants are tolerant to the herbicide Liberty™. Tolerance to Liberty™ can be tested in different ways. The leaf paint method as described herein, is most useful when discrimination between resistant and sensitive plants is required, without killing the sensitive ones. Alternatively, tolerance can be tested by Liberty™ spray application. Spray treatments should be made between the leaf stages V3 and V4 for best results. Tolerant plants are characterized by the fact that spraying of the plants with at least 200 grams active ingredient/hectare (g.a.i./ha), preferably 400 g.a.i./ha, and possibly up to 1600 g.a.i./ha (4× the normal field rate), does not kill the plants. A broadcast application should be applied at a rate of 28-34 oz Liberty™. It is best to apply at a volume of 20 gallons of water per acre using a flat fan type nozzle while being careful not to direct spray applications directly into the whorl of the plants to avoid surfactant burn on the leaves. The herbicide effect should appear within 48 hours and be clearly visible within 5-7 days.

Plants harboring A2704-12 can further be characterized by the presence in their cells of phosphinothricin acetyl transferase as determined by a PAT assay (De Block et al, 1987).

Plants harboring A2704-12 are also characterized by having agronomical characteristics that are comparable to commercially available varieties of soybean in the US, in the absence of weed pressure and use of Liberty™ for weed control. It has been observed that the presence of a foreign DNA in the insertion region of the soybean plant genome described herein, confers particularly interesting phenotypic and molecular characteristics to the plants comprising this event. More specifically, the presence of the foreign DNA in this particular region in the genome of these plants, results in plants which display a stable phenotypic expression of the gene of interest without significantly compromising any aspect of desired agronomic performance of the plants.

The following examples describe the identification of the development of tools for the identification of elite event A2704-12 in biological samples.

Unless otherwise stated, all recombinant DNA techniques are carried out according to standard protocols as described in Sambrook et al. (1989) *Molecular Cloning: A Laboratory Manual*, Second Edition, Cold Spring Harbour Laboratory Press, NY and in Volumes 1 and 2 of Ausubel et al. (1994) *Current Protocols in Molecular Biology*, Current Protocols, USA. Standard materials and methods for plant molecular work are described in Plant Molecular Biology Labfax (1993) by R. D. D. Croy published by BIOS Scientific Publications Ltd (UK) and Blackwell Scientific Publications, UK.

In the description and examples, reference is made to the following sequences:
SEQ ID No. 1: nucleotide sequence comprising a 5' flanking region of A2704-12
SEQ ID No. 2: nucleotide sequence comprising a 3' flanking region of A2704-12
SEQ ID No. 3: primer HCA148
SEQ ID No. 4: primer DPA021
SEQ ID No. 5: primer KVM176
SEQ ID No. 6: primer KVM174
SEQ ID No. 7: primer KVM177
SEQ ID No. 8: primer DPA024
SEQ ID No. 9: primer MDB390
SEQ ID No. 10: primer HCA023
SEQ ID No. 11: primer DPA007
SEQ ID No. 12: primer YTP007
SEQ ID No. 13: primer MDB452
SEQ ID No. 14: primer HCA014
SEQ ID No. 15: primer MDB402
SEQ ID No. 16: primer HCA074
SEQ ID No. 17: primer SMO017
SEQ ID No. 18: primer SMO027
SEQ ID No. 19: primer SMO033
SEQ ID No. 20: primer 1 for amplification of control fragment
SEQ ID No. 21: primer 2 for amplification of control fragment

BRIEF DESCRIPTION OF THE DRAWINGS

The following Examples, not intended to limit the invention to specific embodiments described, may be understood in conjunction with the accompanying Figure, incorporated herein by reference, in which.

EXAMPLES

Figure 1:
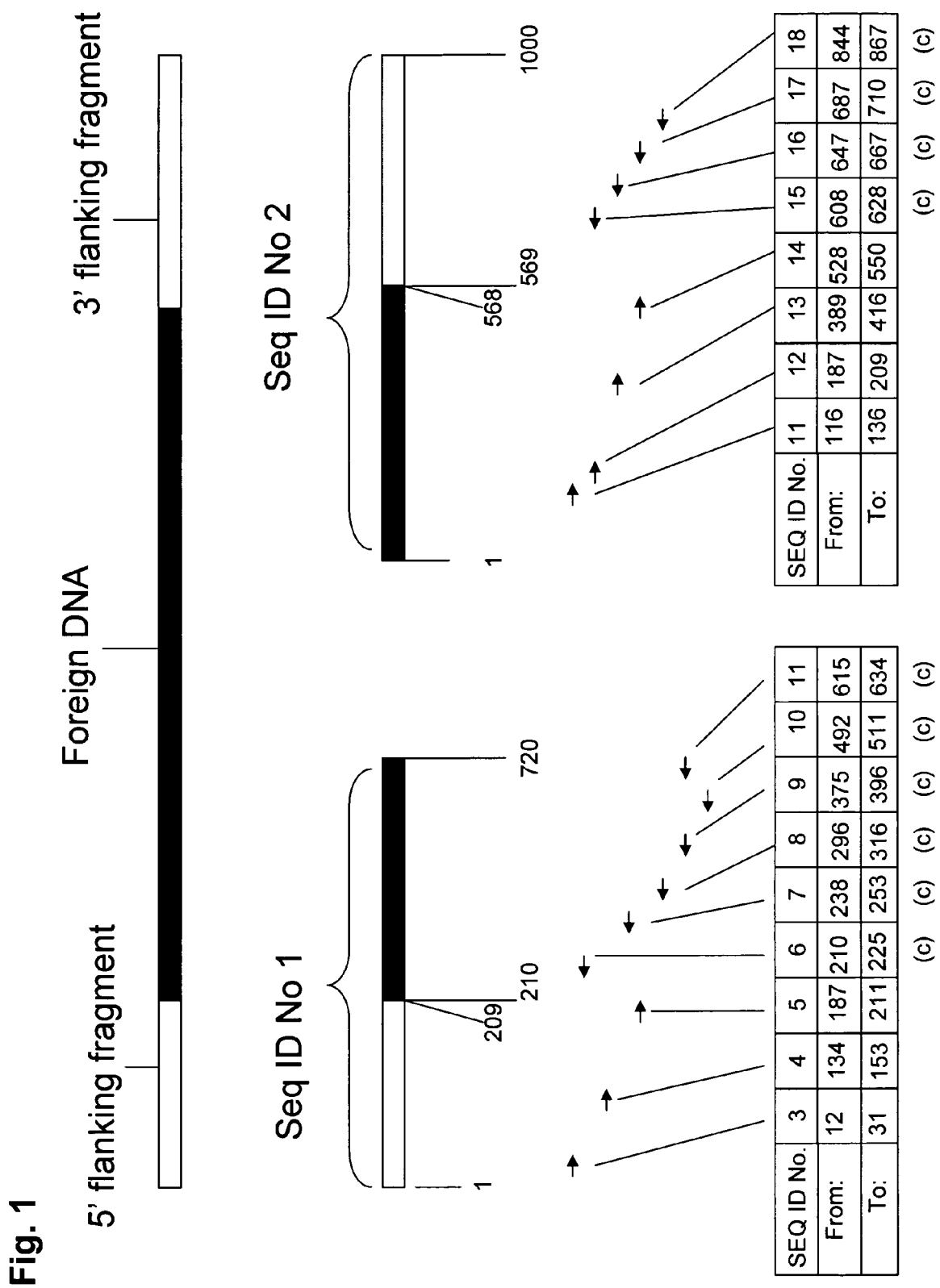
FIG. 1: Schematic representation of the relationship between the cited nucleotide sequences and primers. black bar: foreign DNA; light bar: DNA of plant origin; the figures under the bars represent nucleotide positions; (c) refers to complement of the indicated nucleotide sequence.

1. Identification of the Flanking Regions of Elite Event A2704-12

Herbicide-resistant soybean was developed by transformation of soybean with a vector comprising the coding sequence of a pat gene encoding the enzyme phosphinothricin-acetyl-transferase, under the control of the constitutive 35S promoter from Cauliflower Mosaic virus.

Elite event A2704-12 was selected based on an extensive selection procedure based on good expression and stability of the herbicide resistance gene and its compatibility with optimal agronomic characteristics.

The sequence of the regions flanking the foreign DNA in the A2704-12 event was determined using the thermal asymmetric interlaced (TAIL-) PCR method described by Liu et al. (1995, Plant J. 8(3):457-463). This method utilizes three nested primers in successive reactions together with a shorter arbitrary degenerate primer so that the relative amplification efficiencies of specific and non-specific products can be thermally controlled. The specific primers were selected for annealing to the border of the foreign DNA and based on their annealing conditions. A small amount (5 μl) of unpurified, secondary and tertiary, PCR products were analyzed on a 1% agarose gel. The tertiary PCR product was used for preparative amplification, purified and sequenced on an automated sequencer using the DyeDeoxy Terminator cycle kit.

1.1. Right (5') Flanking Region

The fragment identified as comprising the 5' flanking region obtained by the TAIL-PCR method was completely sequenced (SEQ ID No. 1). The sequence between nucleotide 1 and 209 corresponds to plant DNA, while the sequence between nucleotide 210 and 720 corresponds to foreign DNA.

1.2. Left (3') Flanking Region

The fragment identified as comprising the 3' flanking region obtained by the TAIL-PCR method was completely sequenced (SEQ ID No. 2). The sequence between nucleotide 1 and 568 corresponds to foreign DNA, while the sequence between nucleotide 569 and 1000 corresponds to plant DNA.

2. Development of a Polymerase Chain Reaction Identification Protocol 2.1. Primers Specific primers were developed which recognize sequences within the elite event. More particularly, a primer was developed which recognizes a sequence within the 5' flanking region of A2704-12. A second primer was then selected within the sequence of the foreign DNA so that the primers span a sequence of about 183 nucleotides. The following primers were found to give particularly clear and reproducible results in a PCR reaction on A2704-12 DNA:

```
                                        (SEQ ID No.: 4)
DPA021:    5'- ggC.gTT.CgT.AgT.gAC.TgA.gg -3'
           (target: plant DNA)

(SEQ ID No.: 8)
DPA024:    5'-gTT.TTA.CAA.CgT.gAC.Tgg-3'
           (target: insert DNA)
```

Primers targeting an endogenous sequence are preferably included in the PCR cocktail. These primers serve as an internal control in unknown samples and in the DNA positive control. A positive result with the endogenous primer-pair demonstrates that there is ample DNA of adequate quality in the genomic DNA preparation for a PCR product to be generated. The endogenous primers were selected to recognize a housekeeping gene in *Glycine max*:

```
                                       (SEQ ID No.: 20)
SOY01:     5'-gTC.AgC.CAC.ACA.gTg.CCT.AT-3'
           (located in Glycine max actin 1 gene
           (Accession J01298))

(SEQ ID No.: 21)
SOY02:     5'-gTT.ACC.gTA.CAg.gTC.TTT.CC-3'
           (located in Glycine max actin 1 gene
           (Accession J01298))
```

2.2. Amplified Fragments

The expected amplified fragments in the PCR reaction are:

For primer pair SOY01-SOY02: 413 bp (endogenous control)

For primer pair DPA021-DPA024: 185 bp (A2704-12 elite Event)

2.3. Template DNA

Template DNA was prepared from a leaf punch according to Edwards et al. (Nucleic Acid Research, 19, p 1349, 1991). When using DNA prepared with other methods, a test run utilizing different amounts of template should be done. Usually 50 ng of genomic template DNA yields the best results.

2.4. Assigned Positive and Negative Controls

To avoid false positives or negatives, it was determined that the following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

A wild-type DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

2.5. PCR Conditions

Optimal results were obtained under the following conditions:

the PCR mix for 25 µl reactions contains:
  2.5 µl template DNA
  2.5 µl 10×Amplification Buffer (supplied with Taq polymerase)
  0.5 µl 10 mM dNTP's
  0.5 µl DPA021 (10 pmoles/µl)
  0.5 µl DPA024 (10 pmoles/µl)
  0.25 µl SOY01 (10 pmoles/µl)
  0.25 µl SOY02 (10 pmoles/µl)
  0.1 µl Taq DNA polymerase (5 units/µl)
  water up to 25 µl the thermocycling profile to be followed for optimal results is the following:

|  | |
|---|---|
|  | 4 min. at 95° C. |
| Followed by: | 1 min. at 95° C. |
|  | 1 min. at 57° C. |
|  | 2 min. at 72° C. |
|  | For 5 cycles |
| Followed by: | 30 sec. at 92° C. |
|  | 30 sec. at 57° C. |
|  | 1 min. at 72° C. |
|  | For 25 cycles |
| Followed by: | 5 minutes at 72° C. |

2.6. Agarose Gel Analysis

To optimally visualise the results of the PCR it was determined that between 10 and 20 µl of the PCR samples should be applied on a 1.5% agarose gel (Tris-borate buffer) with an appropriate molecular weight marker (e.g. 100 bp ladder PHARMACIA).

2.7. Validation of the Results

It was determined that data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

When following the PCR Identification Protocol for A2704-12 as described above, lanes showing visible amounts of the transgenic and endogenous PCR products of the expected sizes, indicate that the corresponding plant from which the genomic template DNA was prepared, has inherited the A2704-12 elite event. Lanes not showing visible amounts of either of the transgenic PCR products and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

2.8. Use of Discriminating PCR Protocol to Identify A2704-12

Before attempting to screen unknowns, a test run, with all appropriate controls, has to be performed. The developed protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

*Glycine max* leaf material from a number of plants, some of which comprising A2704-12 were tested according to the above-described protocol. Samples from elite event A2704-12 and from *Glycine max* wild-type were taken as positive and negative controls, respectively.

Figure 2:
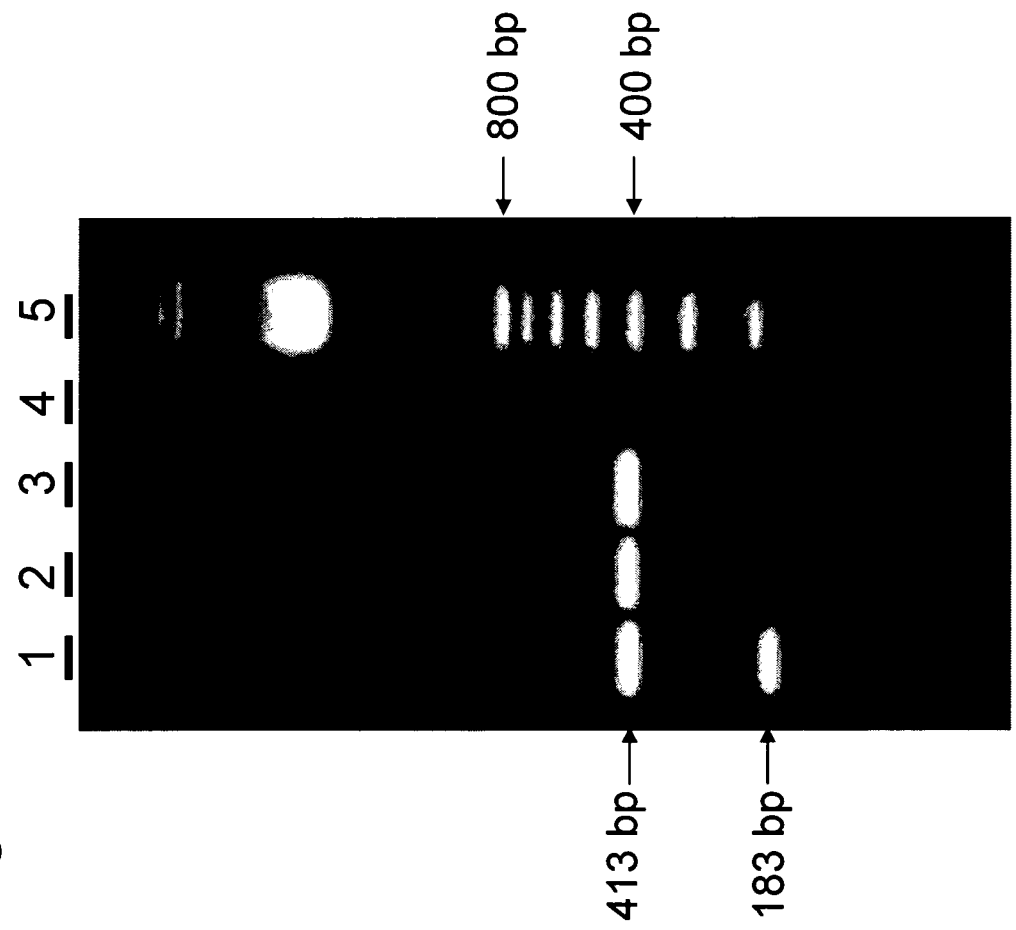
FIG. 2: PCR Identification protocol developed for A2704-12. Loading sequence of the gel: Lane 1: DNA sample from soybean plants comprising the transgenic event A2704-12; lane 2: DNA sample from a transgenic soybean plant not comprising elite event A2704-12; lane 3: control DNA samples from wild-type soybean plants; lane 4: no template control; lane 5: molecular weight marker.

FIG. 2 illustrates the result obtained with the elite event PCR identification protocol for A2704-12 on a number of soybean plant samples (lanes 1 to 14). The samples in lane 1 were found to contain the elite event as the 185 bp band is detected, while the samples in lanes 2, 3 and 4 do not comprise A2704-12. Lane 2 comprises another soybean elite event, lane 3 represents a non-transgenic *Glycine max* control; lane 4 represents the negative control (water) sample, and lane 5 represents the Molecular Weight Marker (100 bp).

3. Use of a Specific Integration Fragment as a Probe for Detection of Material Comprising A2704-12

A specific integration fragment of A2704-12 is obtained by PCR amplification using specific primers DPA021 (SEQ ID No. 4) and DPA024 (SEQ ID No. 8) or by chemical synthesis and is labeled. This integration fragment is used as a specific probe for the detection of A2704-12 in biological samples. Nucleic acid is extracted from the samples according to standard procedures. This nucleic acid is then contacted with the specific probe under hybridization conditions which are optimized to allow formation of a hybrid. The formation of the hybrid is then detected to indicate the presence of A2704-12 nucleic acid in the sample. Optionally, the nucleic acid in the samples is amplified using the specific primers prior to contact with the specific probe. Alternatively, the nucleic acid is labeled prior to contact with the specific probe instead of the integration fragment. Optionally, the specific probe is attached to a solid carrier (such as, but not limited to a filter, strip or beads), prior to contact with the samples.

The invention claimed is:

1. A set of reagents for the specific identification of elite event A2704-12 in biological samples, wherein said elite event has a 5' flanking region and inserted foreign DNA contiguous therewith, and a 3' flanking region and inserted foreign DNA contiguous therewith, said set of reagents comprising a first primer recognizing the 5' flanking region of A2704-12, said 5' flanking region having the nucleotide sequence of SEQ ID No 1 from nucleotide 1 to nucleotide 209 or recognizing the 3' flanking region of A2704-12, said 3' flanking region having the nucleotide sequence of the complement of SEQ ID No 2 from nucleotide 569 to nucleotide 1000, and second primer recognizing a sequence within the foreign DNA, said foreign DNA having the nucleotide sequence of the complement of SEQ ID No. 1 from nucleotide 210 to nucleotide 720 or the nucleotide sequence of SEQ ID No 2 from nucleotide 1 to nucleotide 568, wherein the 5' end of at least one of said primers comprises one or more mismatches or a nucleotide sequence unrelated to the 5' or 3' flanking sequence or foreign DNA sequence.

2. The set of reagents of claim 1, wherein said primer recognizing the 5' flanking region consists at its 3' end of a nucleotide sequence of 17 to 200 consecutive nucleotides selected from the nucleotide sequence of SEQ ID No 1 from nucleotide 1 to nucleotide 209 or said primer recognizing the 3' flanking region of A2704-12 consists at its 3' end of a nucleotide sequence of 17 to 200 consecutive nucleotides selected from the nucleotide sequence of the complement of SEQ ID No 2 from nucleotide 569 to nucleotide 1000, and said primer recognizing a sequence within the foreign DNA consists at its 3' end of 17 to 200 consecutive nucleotides selected from the nucleotide sequence of the complement of SEQ ID No. 1 from nucleotide 210 to nucleotide 720 or the nucleotide sequence of SEQ ID No 2 from nucleotide 1 to nucleotide 568.

3. The set of reagents of claim 1, wherein said primer recognizing the 5' flanking region comprises at its extreme 3' end a nucleotide sequence of at least 17 consecutive nucleotides selected from the nucleotide sequence of SEQ ID No 1 from nucleotide 1 to nucleotide 209 or said primer recognizing the 3' flanking region of A2704-12 comprises at its extreme 3' end a nucleotide sequence of at least 17 consecutive nucleotides selected from the nucleotide sequence of the complement of SEQ ID No 2 from nucleotide 569 to nucleotide 1000, and said primer recognizing a sequence within the foreign DNA comprises at its 3' end at least 17 consecutive nucleotides selected from the nucleotide sequence of the complement of SEQ ID No. 1 from nucleotide 210 to nucleotide 720 or the nucleotide sequence of SEQ ID No 2 from nucleotide 1 to nucleotide 568.

4. The set of reagents of claim 1, comprising a primer consisting at its 3' end of the sequence of SEQ ID No. 4 and a primer consisting at its 3' end of the sequence of SEQ ID No. 8.

5. A set of reagents for the specific identification of elite event A2704-12 in biological samples, said set of reagents comprising a specific probe, capable of hybridizing specifically to a specific region of A2704-12, wherein said specific region comprises a 5' flanking region and inserted foreign DNA contiguous therewith or comprises a 3' flanking region and inserted foreign DNA contiguous therewith, and wherein said 5' flanking region comprises the nucleotide sequence of SEQ ID No. 1 from nucleotide 1 to nucleotide 209, the inserted foreign DNA contiguous therewith comprises the sequence of SEQ ID No. 1 from nucleotide 210 to nucleotide 720, said 3' flanking region comprising the nucleotide sequence of SEQ ID No. 2 from nucleotide 569 to nucleotide 1000, and the inserted foreign DNA contiguous therewith comprising the nucleotide sequence of SEQ ID No. 2 from nucleotide 1 to nucleotide 568, wherein said probe comprises part of the 5' flanking sequence and part of the sequence of the foreign DNA contiguous therewith, or the complement thereof, or part of the 3' flanking sequence and part of the sequence of the foreign DNA contiguous therewith, or the complement thereof.

6. The set of reagents of claim 5, wherein the sequence of said specific probe has at least 80% sequence identity with a sequence comprising part of the 5' flanking sequence or the 3' flanking sequence of A2704-12 and the sequence of the foreign DNA contiguous therewith.

7. The set of reagents of claim 6, wherein the sequence of said specific probe has at least 80% sequence identity with SEQ ID No. 1 from nucleotide 160 to 260 or SEQ ID No. 2 from nucleotide 520 to 620, or the complement of said sequences.

8. A specific probe for the identification of elite event A2704-12 in biological samples, wherein said elite event has a specific region comprising a 5' flanking region and inserted foreign DNA contiguous therewith and a specific region comprising a 3' flanking region and inserted foreign DNA contiguous therewith, and wherein said 5' flanking region comprises the nucleotide sequence of SEQ ID No. 1 from nucleotide 1 to nucleotide 209, the inserted foreign DNA contiguous therewith comprises the sequence of SEQ ID No. 1 from nucleotide 210 to nucleotide 720, said 3' flanking region comprising the nucleotide sequence of SEQ ID No. 2 from nucleotide 569 to nucleotide 1000, and the inserted foreign DNA contiguous therewith comprising the nucleotide sequence of SEQ ID No. 2 from nucleotide 1 to nucleotide 568, and further wherein said probe comprises part of the 5' flanking sequence and part of the sequence of the foreign DNA contiguous therewith, or the complement thereof, or part of the 3' flanking sequence and part of the sequence of the foreign DNA contiguous therewith, or the complement thereof.

9. The probe of claim 8 which has at least 80% sequence identity with SEQ ID No. 1 from nucleotide 160 to 260 or SEQ ID No. 2 from nucleotide 520 to 620, or the complement of said sequences.

10. A DNA comprising part of the 5' or 3' flanking sequence of A2704-12 and part of the sequence of the foreign DNA contiguous therewith, said DNA
   (a) comprising a sequence of between 50 and 500 by with at least 80% sequence identity to a DNA comprising the 5' flanking region of the A2704-12 event and the foreign DNA contiguous therewith, wherein said 5' flanking region comprises the nucleotide sequence of SEQ ID No 1 from nucleotide 1 to nucleotide 209, and the foreign DNA contiguous therewith comprises the nucleotide sequence of SEQ ID No. 1 from nucleotide 210 to nucleotide 720;
   (b) comprising a sequence of between 50 and 500 by with at least 80% sequence identity to a DNA comprising the 3' flanking region of the A2704-12 event and the foreign DNA contiguous therewith, wherein said 3' flanking region comprises the nucleotide sequence of SEQ ID No 2 from nucleotide 569 to nucleotide 1000, and the foreign DNA contiguous therewith comprises the nucleotide sequence of SEQ ID No 2 from nucleotide 1 to nucleotide 568; or
   (c) specifically identifying soybean elite event A2704-12, said DNA comprises the nucleotide sequence of a discriminating amplicon obtainable from a nucleic acid sample comprising said elite event by PCR using a primer specifically recognizing a sequence within the 5' or 3' flanking region of the elite event and a primer specifically recognizing the foreign DNA contiguous therewith, wherein said 5' flanking region comprises the nucleotide sequence of SEQ ID No 1 from nucleotide 1 to nucleotide 209, the foreign DNA contiguous therewith comprises the nucleotide sequence of SEQ ID No. 1 from nucleotide 210 to nucleotide 720, and wherein said 3' flanking region comprises the nucleotide sequence of SEQ ID No 2 from nucleotide 569 to nucleotide 1000, and the foreign DNA contiguous therewith comprises the nucleotide sequence of SEQ ID No 2 from nucleotide 1 to nucleotide 568.

11. A DNA comprising part of the 5' or 3' flanking sequence of A2704-12 and part of the sequence of the foreign DNA contiguous therewith, said DNA comprising a sequence of between 50 and 500 by with at least 80% sequence identity to a DNA comprising the 5' flanking region of the A2704-12 event and the foreign DNA contiguous therewith, wherein said 5' flanking region comprises the nucleotide sequence of SEQ ID No. 1 from nucleotide 1 to nucleotide 209, and the foreign DNA contiguous therewith comprises the nucleotide sequence of SEQ ID No. 1 from nucleotide 210 to nucleotide 720.

12. A DNA comprising part of the 5' or 3' flanking sequence of A2704-12 and part of the sequence of the foreign DNA contiguous therewith, said DNA comprising a sequence of between 50 and 500 by with at least 80% sequence identity to a DNA comprising the 3' flanking region of the A2704-12 event and the foreign DNA contiguous therewith, wherein said 3' flanking region comprises the nucleotide sequence of SEQ ID No. 2 from nucleotide 569 to nucleotide 1000, and the foreign DNA contiguous therewith comprises the nucleotide sequence of SEQ ID No. 2 from nucleotide 1 to nucleotide 568.

13. A DNA specifically identifying soybean elite event A2704-12, said DNA comprises the nucleotide sequence of a discriminating amplicon obtainable from a nucleic acid sample comprising said elite event by PCR using a primer specifically recognizing a sequence within the 5' or 3' flanking region of said elite event and a primer specifically recognizing the foreign DNA contiguous therewith, wherein said 5' flanking region comprises the nucleotide sequence of SEQ ID No. 1 from nucleotide 1 to nucleotide 209, the foreign DNA contiguous therewith comprises the nucleotide sequence of SEQ ID No. 1 from nucleotide 270 to nucleotide 720, and wherein said 3' flanking region comprises the nucleotide sequence of SEQ ID No. 2 from nucleotide 569 to nucleotide 1000, and the foreign DNA contiguous therewith comprises the nucleotide sequence of SEQ ID No. 2 from nucleotide 1 to nucleotide 568.

14. The DNA of claim 13, wherein said primer specifically recognizing a sequence within the 5' flanking region comprises at its extreme 3' end the sequence of SEQ ID No. 4, and said primer specifically recognizing the foreign DNA contiguous therewith comprises at its extreme 3' end the sequence of SEQ ID No. 8, and wherein said amplicon is about 185 bp.

15. A DNA comprising the sequence of SEQ ID No. 1 from nucleotide position 134 to nucleotide position 316.

16. A DNA comprising part of the 5' or 3' flanking sequence of A2704-12 and part of the sequence of the foreign DNA contiguous therewith, said DNA comprising a sequence having at least 95% sequence identity to the sequence of SEQ ID No. 1 between nucleotide 160 and 260 or the sequence of SEQ ID No. 2 between nucleotide 520 and 620.

17. A DNA comprising part of the 5' or 3' flanking sequence of A2704-12 and part of the sequence of the foreign DNA contiguous therewith, said DNA binding to a specific region of elite event A2704-12 under the following standard stringency conditions: 1) immobilizing plant genomic DNA fragments on a filter, 2) prehybridizing the filter for 1 to 2 hours at 42° C. in 50% formamide, 5 X SSPE, 2 X Denhardt's reagent and 0.1% SDS, or for 1 to 2 hours at 68° C. in 6 X SSC, 2 X Denhardt's reagent and 0.1% SDS, 3) adding a hybridization probe which has been labeled, 4) incubating for 16 to 24 hours, 5) washing the filter for 20 min. at room temperature in 1X SSC, 0.1% SDS, 6) washing the filter three times for 20 min. each at 68° C. in 0.2 X SSC, 0.1 SDS, and 7) exposing the filter for 24 to 48 hours to X-ray film at -70° C. with an intensifying screen, wherein said specific region comprises a 5' flanking DNA region and inserted foreign DNA contiguous therewith or a 3' flanking DNA region and inserted foreign DNA contiguous therewith, said 5' flanking DNA region comprising the nucleotide sequence of SEQ ID No 1 from nucleotide 1 to nucleotide 209, said foreign DNA region contiguous with said 5' flanking region comprising the nucleotide sequence of SEQ ID No. 1 from nucleotide 210 to nucleotide 720, said 3' flanking DNA region comprising the nucleotide sequence of SEQ ID No 2 from nucleotide 569 to nucleotide 1000, and said foreign DNA region contiguous with said 3' flanking region comprising the nucleotide sequence of SEQ ID No 2 from nucleotide 1 to nucleotide 568.

18. The DNA of claim 16, said DNA comprising the sequence of SEQ ID No 1 from nucleotide position 160 to nucleotide position 260.

19. The DNA of claim 16, said DNA comprising the sequence of SEQ ID No 2 from nucleotide position 520 to nucleotide position 620.

20. A set of reagents for the specific identification of elite event A2704-12 in biological samples, wherein said elite event has a 5' flanking region and inserted foreign DNA contiguous therewith, and a 3' flanking region and inserted foreign DNA contiguous therewith, said set of reagents comprising a first primer recognizing the 5' flanking region of A2704-12, said 5' flanking region having the nucleotide sequence of SEQ ID No 1 from nucleotide 1 to nucleotide 209 or recognizing the 3' flanking region of A2704-12, said 3' flanking region having the nucleotide sequence of the complement of SEQ ID No 2 from nucleotide 569 to nucleotide 1000, and a second primer recognizing a sequence within the foreign DNA, said foreign DNA having the nucleotide sequence of the complement of SEQ ID No. 1 from nucleotide 210 to nucleotide 720 or the nucleotide sequence of SEQ ID No 2 from nucleotide 1 to nucleotide 568, wherein at least one of said primers comprises at its 3' end a nucleotide sequence spanning the joining region between the plant DNA derived 5' or 3' flanking sequences and the foreign DNA sequences in A2704-12, said joining region being at nucleotides 209-210 in SEQ ID No 1 or nucleotides 568-569 in SEQ ID No 2, provided that the 17 nucleotides at the extreme 3'-end are not derived exclusively from either the foreign DNA or plant-derived sequences in SEQ ID No 1 or 2.

21. The set of reagents of claim 20, wherein said primer recognizing a sequence within the foreign DNA consists at its 3' end of 17 to 200 consecutive nucleotides selected from the nucleotide sequence of the complement of SEQ ID No. 1 from nucleotide 210 to nucleotide 720 or the nucleotide sequence of SEQ ID No 2 from nucleotide 1 to nucleotide 568.

22. The set of reagents of claim 20, wherein said primer recognizing a sequence within the foreign DNA comprises at its 3' end at least 17 consecutive nucleotides selected from the nucleotide sequence of the complement of SEQ ID No. 1 from nucleotide 210 to nucleotide 720 or the nucleotide sequence of SEQ ID No 2 from nucleotide 1 to nucleotide 568.

* * * * *

SEQUENCE LISTING

```
<160> NUMBER OF SEQ ID NOS: 21

<210> SEQ ID NO 1
<211> LENGTH: 720
<212> TYPE: DNA
<213> ORGANISM: Artificial Sequence
<220> FEATURE:
<223> OTHER INFORMATION: nucleotide sequence comprising 5' flanking
      region of EE-GM1
<220> FEATURE:
<221> NAME/KEY: misc_feature
<222> LOCATION: (1)..(209)
<223> OTHER INFORMATION: plant DNA
<220> FEATURE:
<221> NAME/KEY: misc_feature
<222> LOCATION: (210)..(720)
<223> OTHER INFORMATION: insert DNA

<400> SEQUENCE: 1
gagaagaaaa aggaaggcat taagagaccc tcctggcaca accctagaca ctctaagatc    60 cttttcaaa  cctgctccca ccatttcgag tcaagagata gataaataga cacatctcat   120
tgcaccgatc gggggcgttc gtagtgactg aggggggtcaa agaccaagaa gtgagttatt   180
tatcagccaa gcattctatt cttcttatgt cggtgcgggc ctcttcgcta ttacgccagc   240
tggcgaaagg gggatgtgct gcaaggcgat taagttgggt aacgccaggg tttcccagt    300 cacgacgttg taaaacgacg gccagtgaat tcccatggag tcaaagattc aaatagagga   360
cctaacagaa ctcgccgtaa agactggcga acagttcata cagagtctct tacgactcaa   420
tgacaagaag aaaatcttcg tcaacatggt ggagcacgac acgcttgtct actccaaaaa   480
```

```
tatcaaagat acagtctcag aagaccaaag gcaattgag actttttcaac aaagggtaat      540 atccggaaac ctcctcggat tccattgccc agctatctgt cactttattg tgaagatagt      600
ggaaaaggaa ggtggctcct acaaatgcca tcattgcgat aaaggaaagg ccatcgttga     660
agatgcctct gccgacagtg gtcccaaaga tggaccccca cccacgagga gcatcgtgga    720
```

<210> SEQ ID NO 2
<211> LENGTH: 1000
<212> TYPE: DNA
<213> ORGANISM: Artificial Sequence
<220> FEATURE:
<223> OTHER INFORMATION: nucleotide sequence comprising 3' flanking
      region of EE-GM1
<220> FEATURE:
<221> NAME/KEY: misc_feature
<222> LOCATION: (1)..(568)
<223> OTHER INFORMATION: insert DNA
<220> FEATURE:
<221> NAME/KEY: misc_feature
<222> LOCATION: (569)..(1000)
<223> OTHER INFORMATION: plant DNA

<400> SEQUENCE: 2

```
ttcggtgtag gtcgttcgct ccaagctggg ctgtgtgcac gaaccccccg ttcagcccga      60
ccgctgcgcc ttatccggta actatcgtct tgagtccaac ccggtaagac acgacttatc     120
gccactggca gcagccactg gtaacaggat tagcagagcg aggtatgtag gcggtgctac     180
agagttcttg aagtggtggc ctaactacgg ctacactaga agaacagtat ttggtatctg     240
cgctctgctg aagccagtta ccttcggaaa aagagttggt agctcttgat ccggcaaaca     300
aaccaccgct ggtagcggtg gttttttttgt ttgcaagcag cagattacgc gcagaaaaaa    360
aggatctcaa gaagatcctt tgatctttc tacggggtct gacgctcagt ggaacgaaaa     420
ctcacgttaa gggattttgg tcatgagatt atcaaaaagg atcttcacct agatcctttt    480
aaattaaaaa tgaagtttta atcaatcta aagtatatat gagtaaactt ggtctgacag     540
ttaccaatgc ttaatcagtg aggcaccttt aatctagatg atctgtctca actttaccaa   600 aagtttttgag cacatgtttg gattcaccct aaataatcta aaatcacagc ttgtttgatc   660
ccaaaggagt taattctaag taaaattgat tgagttaaaa caattgtgtt agatagaaa    720 attttctttg aataaaaaca tctagacaca aatcatttca cttcaaaata attttaaaca   780
aaataaattt tgcaattcat tcatccaaac aaacatttga attaactata atcaattcaa   840
attgttacag tgtgttgcat tcatatcatt cctaataagt ctacattaaa gattaagagt    900
gagaatgaga ggaagagaga acggtttcag ggttaaccct tgtttggaa gaaccatcaa   960 acagtggcaa cggatcatcc ttgctgcaaa acatagcttt                        1000
```

<210> SEQ ID NO 3
<211> LENGTH: 20
<212> TYPE: DNA
<213> ORGANISM: Artificial Sequence
<220> FEATURE:
<223> OTHER INFORMATION: oligonucleotide primer HCA148

<400> SEQUENCE: 3

```
ggaaggcatt aagagaccct                                                  20
```

<210> SEQ ID NO 4
<211> LENGTH: 20
<212> TYPE: DNA
<213> ORGANISM: Artificial Sequence
<220> FEATURE:

```
<223> OTHER INFORMATION: oligonucleotide primer DPA021

<400> SEQUENCE: 4
ggcgttcgta gtgactgagg                                            20

<210> SEQ ID NO 5
<211> LENGTH: 25
<212> TYPE: DNA
<213> ORGANISM: Artificial Sequence
<220> FEATURE:
<223> OTHER INFORMATION: oligonucleotide primer KVM176

<400> SEQUENCE: 5
ccaagcattc tattcttctt atgtc                                      25

<210> SEQ ID NO 6
<211> LENGTH: 16
<212> TYPE: DNA
<213> ORGANISM: Artificial Sequence
<220> FEATURE:
<223> OTHER INFORMATION: oligonucleotide primer kvm174

<400> SEQUENCE: 6
aagaggcccg caccga                                                16

<210> SEQ ID NO 7
<211> LENGTH: 16
<212> TYPE: DNA
<213> ORGANISM: Artificial Sequence
<220> FEATURE:
<223> OTHER INFORMATION: oligonucleotide primer KVM177

<400> SEQUENCE: 7 cccccttttcg ccagct                                               16

<210> SEQ ID NO 8
<211> LENGTH: 21
<212> TYPE: DNA
<213> ORGANISM: Artificial Sequence
<220> FEATURE:
<223> OTHER INFORMATION: oligonucleotide primer DPA024

<400> SEQUENCE: 8
gttttacaac gtcgtgactg g                                          21

<210> SEQ ID NO 9
<211> LENGTH: 22
<212> TYPE: DNA
<213> ORGANISM: Artificial Sequence
<220> FEATURE:
<223> OTHER INFORMATION: oligonucleotide primer MDB390

<400> SEQUENCE: 9
aactgttcgc cagtctttac gg                                         22

<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer HCA023

<400> SEQUENCE: 10
cctttggtct tctgagactg                                            20
```

-continued

```
<210> SEQ ID NO 11
<211> LENGTH: 20
<212> TYPE: DNA
<213> ORGANISM: Artificial Sequence
<220> FEATURE:
<223> OTHER INFORMATION: oligonucleotide primer DPA007

<400> SEQUENCE: 11
atgatggcat ttgtaggagc                                              20

<210> SEQ ID NO 12
<211> LENGTH: 21
<212> TYPE: DNA
<213> ORGANISM: Artificial Sequence
<220> FEATURE:
<223> OTHER INFORMATION: oligonucleotide primer YPT007

<400> SEQUENCE: 12
ttatcgccac tggcagcagc c                                            21

<210> SEQ ID NO 13
<211> LENGTH: 23
<212> TYPE: DNA
<213> ORGANISM: Artificial Sequence
<220> FEATURE:
<223> OTHER INFORMATION: MDB452

<400> SEQUENCE: 13
cttgaagtgg tggcctaact acg                                          23

<210> SEQ ID NO 14
<211> LENGTH: 19
<212> TYPE: DNA
<213> ORGANISM: Artificial Sequence
<220> FEATURE:
<223> OTHER INFORMATION: oligonucleotide primer HCA014

<400> SEQUENCE: 14
tctgacgctc agtggaacg                                               19

<210> SEQ ID NO 15
<211> LENGTH: 23
<212> TYPE: DNA
<213> ORGANISM: Artificial Sequence
<220> FEATURE:
<223> OTHER INFORMATION: oligonucleotide primer MDB402

<400> SEQUENCE: 15
cttggtctga cagttaccaa tgc                                          23

<210> SEQ ID NO 16
<211> LENGTH: 21
<212> TYPE: DNA
<213> ORGANISM: Artificial Sequence
<220> FEATURE:
<223> OTHER INFORMATION: oligonucleotide primer HCA074

<400> SEQUENCE: 16
ggtgaatcca aacatgtgct c                                            21

<210> SEQ ID NO 17
<211> LENGTH: 21
<212> TYPE: DNA
<213> ORGANISM: Artificial Sequence
<220> FEATURE:
<223> OTHER INFORMATION: oligonucleotide primer SMO017
```

```
<400> SEQUENCE: 17
cctttgggat caaacaagct g                                         21

<210> SEQ ID NO 18
<211> LENGTH: 24
<212> TYPE: DNA
<213> ORGANISM: Artificial Sequence
<220> FEATURE:
<223> OTHER INFORMATION: oligonucleotide primer SMO027

<400> SEQUENCE: 18
aacacaattg ttttaactca atca                                      24

<210> SEQ ID NO 19
<211> LENGTH: 24
<212> TYPE: DNA
<213> ORGANISM: Artificial Sequence
<220> FEATURE:
<223> OTHER INFORMATION: oligonucleotide primer SMO033

<400> SEQUENCE: 19
gatatgaatg caacacactg taac                                      24

<210> SEQ ID NO 20
<211> LENGTH: 20
<212> TYPE: DNA
<213> ORGANISM: Artificial Sequence
<220> FEATURE:
<223> OTHER INFORMATION: oligonucleotide primer SOY01

<400> SEQUENCE: 20
gtcagccaca cagtgcctat                                           20

<210> SEQ ID NO 21
<211> LENGTH: 20
<212> TYPE: DNA
<213> ORGANISM: Artificial Sequence
<220> FEATURE:
<223> OTHER INFORMATION: oligonucleotide primer SOY02

<400> SEQUENCE: 21
gttaccgtac aggtctttcc                                           20
```